(12) United States Patent
Rosenberg et al.

(10) Patent No.: US 11,628,171 B2
(45) Date of Patent: Apr. 18, 2023

(54) METHOD FOR TREATING BRAIN OR NERVE INJURY

(71) Applicant: CHILDREN'S MEDICAL CENTER CORPORATION, Boston, MA (US)

(72) Inventors: Paul Rosenberg, Boston, MA (US); Larry Benowitz, Boston, MA (US)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 156 days.

(21) Appl. No.: 16/816,870

(22) Filed: Mar. 12, 2020

(65) Prior Publication Data

US 2020/0289518 A1 Sep. 17, 2020

Related U.S. Application Data

(60) Provisional application No. 62/817,896, filed on Mar. 13, 2019.

(51) Int. Cl.
| | | |
|---|---|---|
| *A61K 31/519* | (2006.01) | |
| *A61K 9/00* | (2006.01) | |
| *A61P 25/00* | (2006.01) | |
| *A61P 27/02* | (2006.01) | |

(52) U.S. Cl.
CPC .......... *A61K 31/519* (2013.01); *A61K 9/0019* (2013.01); *A61K 9/0048* (2013.01); *A61P 25/00* (2018.01); *A61P 27/02* (2018.01)

(58) Field of Classification Search
CPC ........................... A61K 31/519; A61K 31/517
See application file for complete search history.

(56) References Cited

U.S. PATENT DOCUMENTS

| 9,073,936 | B2 | 7/2015 | Li et al. | |
|---|---|---|---|---|
| 9,545,406 | B2 * | 1/2017 | Wennogle | ............ A61K 31/517 |
| 2008/0188492 | A1 | 8/2008 | Li et al. | |
| 2010/0173878 | A1 | 7/2010 | Li et al. | |
| 2010/0273753 | A1 | 10/2010 | Li | |
| 2010/0273754 | A1 | 10/2010 | Li | |
| 2014/0148421 | A1 | 5/2014 | Li et al. | |
| 2021/0213018 | A1 * | 7/2021 | Snyder | ................ A61K 31/519 |

FOREIGN PATENT DOCUMENTS

| WO | 2010065147 A1 | 6/2010 |
|---|---|---|
| WO | 2010065149 A1 | 6/2010 |
| WO | 2010065151 A1 | 6/2010 |
| WO | 2010065152 A1 | 6/2010 |
| WO | 2010065153 A1 | 6/2010 |
| WO | 2011133224 A1 | 10/2011 |
| WO | 2011153129 A1 | 12/2011 |
| WO | 2011153135 A1 | 12/2011 |
| WO | 2011153136 A1 | 12/2011 |
| WO | 2011153138 A1 | 12/2011 |
| WO | 2018049417 A1 | 3/2018 |

OTHER PUBLICATIONS

Abdul Amin et al., Journal of Biomolecular Structure and Dynamics(2018), 36(3), 590-608.*

Yin et al., "Oncomodulin links inflammation to optic nerve regeneration," Proceedings of the National Academy of Sciences USA; 2009, vol. 106, No. 46, pp. 19587-19592 (6 pages).

* cited by examiner

*Primary Examiner* — Paul V Ward
(74) *Attorney, Agent, or Firm* — Melissa Hunter-Ensor; Leslie Serunian; Greenberg Traurig, LLP

(57) ABSTRACT

The invention provides a method for treating brain or nerve injury.

5 Claims, 1 Drawing Sheet

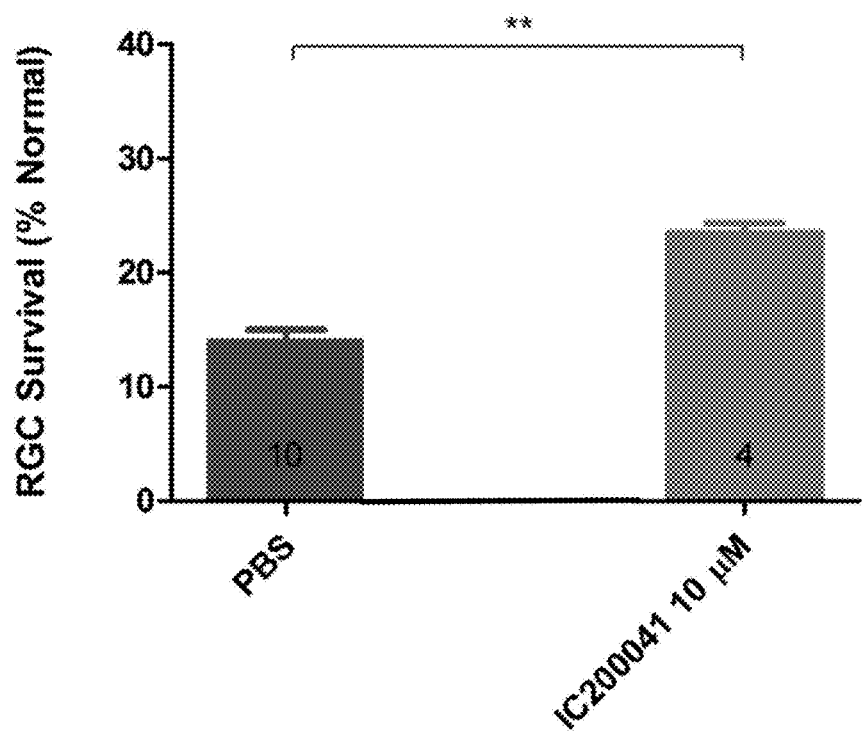
** p < 0.001 One-way ANOVA
with Bonferroni post-hoc test

METHOD FOR TREATING BRAIN OR NERVE INJURY

CROSS REFERENCE TO RELATED APPLICATION

The application claims priority to and benefit of U.S. Provisional Application No. 62/817,896, filed on Mar. 13, 2019, the contents of which are hereby incorporated by reference in their entirety.

STATEMENT OF RIGHTS TO INVENTIONS MADE UNDER FEDERALLY SPONSORED RESEARCH

This invention was made with government support under Grant Numbers EY027881 and EY024481, awarded by The National Institutes of Health; and under Grant Number W81XWH11-2-0023, awarded by the U.S. Department of the Army. The government has certain rights in the invention.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), are activated by the $Ca^{2+}$-calmodulin and have been shown to mediate the calcium and cyclic nucleotide (e.g. cAMP and cGMP) signaling pathways. These PDEs are therefore active in stimulated conditions when intra-cellular calcium levels rise, leading to increased hydrolysis of cyclic nucleotides. The three known CaM-PDE genes, PDE1A, PDE1B, and PDE1C, are all expressed in central nervous system tissue. In the brain, the predominant expression of PDE1A is in the cortex and neostriatum, PDE1B is expressed in the neostriatum, prefrontal cortex, hippocampus, and olfactory tubercle, and PDE1C is more ubiquitously expressed.

PDE4 is the major cAMP-metabolizing enzyme found in inflammatory and immune cells, and PDE4 inhibitors are of interest as anti-inflammatory drugs. PDE1, however, has not been thought to play a major role in the inflammatory response, although PDE-1 is induced in monocyte-to-macrophage differentiation mediated by the cytokine granulocyte-macrophage colony-stimulating factor (GM-CSF). The PDE1 inhibitor vinpocetine has been shown to be anti-inflammatory, but the anti-inflammatory action of vinpocetine is believed to be caused by a direct inhibition of the IκB kinase complex (IKK) rather than PDE blockade.

Microglia have a central role in maintaining homeostasis and mediating inflammation in the brain. Microglia communicate with complex signaling to neurons and astrocytes, determining how many brains cells are needed and when to eliminate a synapse, e.g., destroying the defective or unused synapses. Microglia may exist in different states: a resting state, which is relatively inactive but may perform surveillance functions, or in one of two functionally distinct activation states, M1 and M2. The M1 state is induced by a signal such as IFN-γ or lipopolysaccharide (LPS), and responds by releasing inflammatory cytokines such as TNF-, IL-1β, and reactive oxygen species/reactive nitrogen species (ROS/NOS). The M2 state has an anti-inflammatory effect, blocking the release of pro-inflammatory cytokines, ingesting debris, promoting tissue repair and releasing neurotrophic factors. Activated microglia have been associated with a variety of neurodegenerative diseases including Alzheimer's disease (AD), Parkinson's disease (PD) and amyotrophic lateral sclerosis (ALS), and may contribute to the pathology of these diseases, although it is not conclusively determined whether inflammation is an underlying cause or an effect of these conditions.

It has not been previously shown that PDE1 has a significant role in mediating inflammatory cytokines, in the brain or elsewhere, or that it would have a significant effect on inflammatory diseases. Inflammatory processes in general, and diseases and disorders related to inflammation, are numerous, and the mechanisms and actions are still not well understood. Currently, there is a largely unmet need for an effective way of treating inflammation and inflammatory related diseases and disorders, especially with regard to inflammation occurring in the brain.

BRIEF DESCRIPTION OF DRAWINGS

FIG. 1 presents a graph which demonstrates that the tested PDE1 inhibitor is highly effective in increasing the survival of retinal ganglion cells when compared with the PBS control in the optic injury model described in Example 1 infra.

SUMMARY OF THE INVENTION

Surprisingly, we have discovered that PDE1 mediates the expression of certain pro-inflammatory cytokines and chemokines and that PDE1 inhibitors have specific anti-inflammatory effects, which are different from the anti-inflammatory effects of PDE4 inhibitors. In one aspect, inhibition of PDE1 regulates inflammatory activity in microglia, reducing expression of pro-inflammatory genes, with a profile different from PDE4 inhibition, thereby providing novel treatments for toxic neuroinflammation.

Negative regulation of inflammatory responses in microglia by elevated intracellular cyclic nucleotide levels provides a promising area for therapeutic intervention. Cyclic guanosine monophosphate (cGMP) in microglia is produced by activation of atrial natriuretic receptors or soluble guanylyl cyclase and is hydrolyzed by phosphodiesterases (PDEs). Increasing intracellular cGMP by either stimulating production or inhibiting hydrolysis has been shown to attenuate LPS-induced responses in microglia. Additionally, cGMP has been shown to play a role in LPS-induced motility of microglia. Cyclic adenosine monophosphate (cAMP) is also a key regulator of inflammatory responses. LPS and cytokine stimulation have been shown to increase expression of PDE4B and decrease cAMP. PDEs are proven drug-able targets. Enzymes of the PDE1 family, of which PDE1B is expressed in microglia, hydrolyze both cAMP and cGMP and are activated by calcium.

Among the roles played by the PDE1 enzyme targets of the compounds of the invention, the PDE1B isoform is found in high abundance in microglia, where it may play a role in controlling inflammatory responses, in particular under conditions of elevated intracellular calcium. This suggests that ITI-214 might prove beneficial in diseases associated with, for example, chronic neuroinflammation.

In one embodiment, therefore, the invention provides using various PDE1 inhibitory compounds to treat inflammation, and/or diseases or disorders related to inflammation. Inflammation can be neuroinflammation, and in one embodiment the PDE1 inhibitors can specifically modulate microglial activation in the brain. We have surprisingly discovered that the LPS-induced expression of certain inflammatory biomarkers (e.g., IL1β, TNF-α, and Ccl2) can be blunted or decreased with the administration of a PDE1 inhibitor as described herein. This discovery has wide-ranging applications for treating inflammatory diseases and disorders related or correlated to the expression of various inflammatory biomarkers.

Without being bound by theory, one possible mechanism for this activity is that inhibition of PDE1B may affect macrophage activation in the blood and/or microglial activation in the CNS, so as to reduce M1 activation and the release of pro-inflammatory cytokines, and to enhance the action of M2 microglia, through the up-regulation of anti-inflammatory cytokines such as IL-10. The role of neuroinflammation and microglial function in CNS pathologies is not fully understood, but we hypothesize that it is relevant to a variety of conditions, including:

a. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;
b. repair of damage due to stroke, cardiac arrest, hypoxia, intracerebral hemorrhage or traumatic brain injury;
c. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation;
d. chronic CNS infections, e.g., Lyme disease, syphilis, or CNS infection consequent to an immunosuppressive condition, e.g., HIV dementia;
e. neuroinflammation consequent to chemotherapy.

Targeted inhibition of PDE1 in the brain with a compound of the present invention is believed to affect microglial activation and reduce damaging pro-inflammatory cytokine signaling, and at the same time, increasing production of anti-inflammatory cytokines and factors involved in microglia motility and recruitment.

Accordingly, in one embodiment, the invention provides a new method of treatment or prophylaxis of inflammation or disease associated with inflammation that may be ameliorated by administration of a specific inhibitor of phosphodiesterase type I (e.g., PDE1 inhibitor, e.g., a PDE1B inhibitor) (e.g., a PDE1 inhibitor of Formula I, II, III, IV, V, VI, VII, VIII, IX, X, XI, and/or XII as herein described).

In one embodiment the invention provides a method of treating neuroinflammation and/or diseases or disorders associated with neuroinflammation and/or microglial function, e.g., selected from:

f. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;
g. stroke, cardiac arrest, hypoxia, intracerebral hemorrhage or traumatic brain injury;
h. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation; and
i. chronic CNS infections, e.g., Lyme disease or CNS infection consequent to an immunosuppressive condition, e.g., HIV-dementia;
j. neuroinflammation consequent to chemotherapy;

comprising administering an effective amount of a PDE1 inhibitor of the current invention (e.g., a PDE1 inhibitor of Formula I, II, III, IV, V, VI, VII, VIII, IX, X, XI, and/or XII as herein described), e.g., an amount effective to (i) reduce or inhibit activation of M1 microglia, and/or (ii) and amount effective to reduce levels of one or more pro-inflammatory cytokines (e.g., IL1β, TNF-α, and Ccl2, or combination thereof); to a patient in need thereof.

In one embodiment PDE1 inhibitors of the current invention (e.g., a PDE1 inhibitor of Formula I, II, III, IV, V, VI, VII, VIII, IX, X, XI, and/or XII as herein described) are administered to a patient with increased levels of one or more pro-inflammatory cytokines (e.g., IL1β, TNF-α, and Ccl2, or combination thereof), e.g., to a patient suffering from neuroinflammation and/or diseases or disorders associated with neuroinflammation and/or microglial function, e.g., selected from:

k. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;
l. stroke, cardiac arrest, hypoxia, intracerebral hemorrhage or traumatic brain injury;
m. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation; and
n. chronic CNS infections, e.g., Lyme disease or CNS infection consequent to an immunosuppressive condition, e.g., HIV-dementia;
o. neuroinflammation consequent to chemotherapy.

In an aspect, a method for treating brain or nerve injury in a subject is provided, in which the method comprises administering to a patient in need thereof an effective amount of a PDE1 inhibitor sufficient to increase cell survival, thereby treating brain or nerve injury. In an embodiment, the PDE1 inhibitor is IC200041. In an embodiment, the method increases the survival of retinal ganglion cells.

In an aspect, a method for increasing axonal regeneration following nerve injury is provided, in which the method comprises administering to a patient in need thereof an effective amount of IC200041, thereby increasing axonal regeneration following nerve injury. In an embodiment, the nerve injury is optic nerve injury or retinal insult. In an embodiment, the administration is by injection. In an embodiment, the administration is by intraocular injection.

In an aspect, a method for promoting axonal regeneration in an injured neuron is provided, in which the method comprises contacting the injured neuron with an effective amount of a PDE1 inhibitor before or following injury, thereby promoting axonal regeneration in the neuron. In an embodiment, the neuron is in vitro or in vivo.

In an aspect, method for promoting neuronal survival and regeneration in connection with CNS injury in a subject is provided, in which the method comprises administering an effective amount of a PDE1 inhibitor to a subject in need thereof, thereby increasing neuronal survival and regeneration relative to a reference, e.g., a standard of comparison or control condition, as would be understood by the skilled practitioner in the art. In an embodiment, the administering is prior to, concurrent with, or subsequent to the injury in the subject. In an embodiment, the injury is a central nervous system (CNS) injury. In an embodiment, the injury is an optic nerve injury. In an embodiment, neuronal survival is twice the level of survival present in an untreated control subject.

In an embodiment of the methods of the above-delineated aspects, the PDE1 inhibitor hydrolyzes both cGMP and cAMP. In an embodiment of the methods of the above-delineated aspects, the axonal regeneration is nitric oxide dependent. In an embodiment of the methods of the above-delineated aspects, the neuron is a retinal ganglion cell or a neuron present in the optic nerve. In an embodiment of the methods of the above-delineated aspects, the PDE1 inhibitor is administered within about 24 or 72 hours of CNS injury. In an embodiment of the methods of the above-delineated aspects, the PDE1 inhibitor is administered by intraocular injection. In an embodiment, intraocular injections are given at Day 1, Day 2 and Day 3 following injury. In an embodiment, intraocular injections are given about 24 hours prior to injury, within less than about 3 hours of injury, and about three or four days following injury. In an embodiment of the methods of the above-delineated aspects, axon outgrowth is greater than about 0.5 mm from the site of injury. In an embodiment, axon outgrowth is greater than about 1.0 mm from the site of injury.

Further embodiments of the invention are set forth or evident from the detailed description below and the examples herein.

DETAILED DESCRIPTION OF THE INVENTION

Compounds for Use in the Methods of the Invention

In one embodiment, the PDE1 inhibitors for use in the methods of treatment and prophylaxis described herein are optionally substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., a Compound of Formula II, e.g., II-A or II-B: In one embodiment, the PDE1 inhibitors for use in the methods of treatment and prophylaxis described herein are optionally substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., a Compound of Formula II, e.g., II-A or II-B:

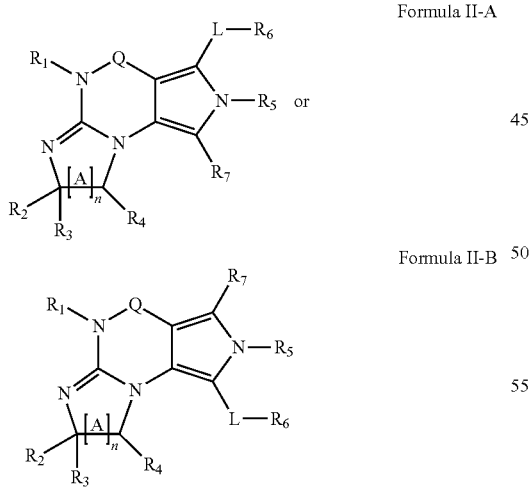

wherein
(i) Q is C(=O), C(=S), C(=N($R_{20}$)) or $CH_2$;
(ii) L is a single bond, —N(H)—, —$CH_2$—, —S—, —S(O)— or —S($O_2$)—;
(iii) $R_1$ is H or $C_{1-4}$ alkyl (e.g., methyl);
(iv) $R_4$ is H or $C_{1-6}$ alkyl (e.g., methyl or isopropyl) and $R_2$ and $R_3$ are, independently,

H $C_{1-6}$ alkyl (e.g., methyl, isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, (optionally hetero)aryl$C_{1-6}$alkyl; or $R_2$ and $R_3$ together form a 3- to 6-membered ring;
or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
or (v) $R_5$ is
  a) -D-E-F, wherein:
     D is $C_{1-4}$ alkylene (e.g., methylene, ethylene or prop-2-yn-1-ylene);
     E is a single bond, $C_{2-4}$ alkynylene (e.g., —C≡C—), arylene (e.g., phenylene) or heteroarylene (e.g., pyridylene);
     F is
        H,
        aryl (e.g., phenyl),
        heteroaryl (e.g., pyridyl, diazolyl, triazolyl, for example, pyrid-2-yl, imidazol-1-yl, 1,2,4-triazol-1-yl),
        halo (e.g., F, Br, Cl),
        halo$C_{1-4}$alkyl (e.g., trifluoromethyl),
        —C(O)—$R_{15}$,
        —N($R_{16}$)($R_{17}$), or
        $C_{3-7}$ cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
     wherein D, E and F are independently and optionally substituted with one or more halo (e.g., F, Cl or Br), $C_{1-4}$ alkyl (e.g., methyl), halo$C_{1-4}$alkyl (e.g., trifluoromethyl), $C_{1-4}$ alkoxy (e.g., methoxy), hydroxy, $C_{1-4}$ carboxy, or an additional aryl or heteroaryl (e.g., biphenyl or pyridylphenyl),
     for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$ alkyl (e.g., 5-methylpyrid-2-yl), or F is aryl, e.g., phenyl, substituted with one or more halo (e.g., 4-fluorophenyl) or F is a $C_{3-7}$ heterocycloalkyl (e.g., pyrrolidinyl) optionally substituted with a $C_{1-6}$alkyl (e.g., 1-methylpyrrolidin-3-yl); or
  b) a substituted heteroarylalkyl, e.g., substituted with halo$C_{1-4}$alkyl;
  c) attached to the nitrogen on the pyrrolo portion of Formula II-A or II-B and is a moiety of Formula A

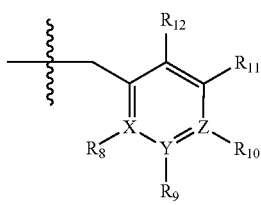

Formula A wherein X, Y and Z are, independently, N or C, and $R_8$, $R_9$, $R_{11}$ and $R_{12}$ are independently H or halogen (e.g., Cl or F), and $R_{10}$ is
halogen,
$C_{1-4}$ alkyl,
halo$C_{1-4}$alkyl (e.g., triflouromethyl)
$C_{1-4}$ alkoxy (e.g. methoxy),
$C_{3-7}$ cycloalkyl,
hetero$C_{3-7}$cycloalkyl (e.g., pyrrolidinyl or piperidinyl),
$C_{1-4}$ haloalkyl (e.g., trifluoromethyl),
aryl (e.g., phenyl),
heteroaryl (e.g., pyridyl (for example pyrid-2-yl or pyrid-4-yl), or thiadiazolyl (e.g., 1,2,3-thiadiazol-4-yl)), diazolyl (e.g., imidazol-1-yl), triazolyl (e.g., 1,2,4-triazol-1-yl), tetrazolyl,
arylcarbonyl (e.g., benzoyl),
alkylsulfonyl (e.g., methylsulfonyl),
heteroarylcarbonyl, or
alkoxycarbonyl;
wherein the aryl, heteroaryl, cycloalkyl or heterocycloalkyl is independently, optionally substituted with one or more $C_{1-4}$ alkyl (e.g., methyl), halogen (e.g., chloro or fluoro), halo$C_{1-4}$alkyl (e.g., trifluoromethyl), hydroxy, $C_{1-4}$ carboxy, —SH or an additional aryl, heteroaryl (e.g., biphenyl or pyridylphenyl) or $C_{3-8}$ cycloalkyl,
preferably $R_{10}$ is phenyl, pyridyl, piperidinyl or pyrrolidinyl optionally substituted with the substituents previously defined, e.g. optionally substituted with halo or alkyl
provided that when X, Y, or Z is nitrogen, $R_8$, $R_9$, or $R_{10}$, respectively, is not present;
(vi) $R_6$ is
H,
$C_{1-4}$ alkyl (e.g., methyl, ethyl, n-propyl, isobutyl),
$C_{3-7}$ cycloalkyl (e.g., cyclopentyl or cyclohexyl),
hetero$C_{3-7}$cycloalkyl (e.g., pyrrolidinyl, piperidinyl, morpholinyl),
aryl (e.g., phenyl),
heteroaryl (e.g., pyrid-4-yl),
aryl $C_{1-4}$ alkyl (e.g., benzyl),
arylamino (e.g., phenylamino),
heteroarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$),
wherein the aryl and heteroaryl are optionally substituted with one or more $C_{1-4}$ alkyl (e.g., methyl), halogen (e.g., chloro or fluoro), halo$C_{1-4}$alkyl (e.g., trifluoromethyl), hydroxy, $C_{1-4}$ carboxy, or an additional aryl, heteroaryl (e.g., biphenyl or pyridylphenyl) or $C_{3-8}$ cycloalkyl;

(vii) $R_7$ is H, $C_{1-6}$alkyl (e.g., methyl or ethyl), halogen (e.g., Cl), —N($R_{18}$)($R_{19}$), hydroxy or $C_{1-6}$ alkoxy;
(viii) n=0 or 1;
(ix) when n=1, A is —C($R_{13}R_{14}$)—, wherein $R_{13}$ and $R_{14}$, are, independently, H or $C_{1-4}$ alkyl, aryl, heteroaryl, (optionally hetero)aryl$C_{1-4}$alkoxy, (optionally hetero)aryl$C_{1-4}$alkyl or $R_{14}$ can form a bridge with $R_2$ or $R_4$;
(x) $R_{15}$ is $C_{1-4}$ alkyl, halo$C_{1-4}$alkyl, —OH or —O$C_{1-4}$alkyl (e.g., —OCH$_3$)
(xi) $R_{16}$ and $R_{17}$ are independently H or $C_{1-4}$ alkyl;
(xii) $R_{18}$ and $R_{19}$ are independently
H,
$C_{1-4}$ alky (e.g., methyl, ethyl, n-propyl, isobutyl),
$C_{3-8}$ cycloalky (e.g., cyclohexyl or cyclopenyl),
hetero $C_{3-8}$ cycloalky (e.g., pyrrolidinyl, piperidinyl, morpholinyl),
aryl (e.g., phenyl) or
heteroaryl (e.g., pyridyl),
wherein said aryl and heteroaryl are optionally substituted with one or more
halo (e.g., fluorophenyl, e.g., 4-fluorophenyl),
hydroxy (e.g., hydroxyphenyl, e.g., 4-hydroxyphenyl or 2-hydroxyphenyl),
$C_{1-4}$ alkyl (e.g., methyl),
halo$C_{1-4}$ alkyl (e.g., trifluoromethyl),
$C_{1-4}$ carboxy, or
an additional aryl, heteroaryl (e.g., biphenyl or pyridylphenyl) or $C_{3-8}$ cycloalkyl,
(xiii) $R_{20}$ is H, $C_{1-4}$ alkyl or $C_{3-7}$ cycloalkyl;
in free or salt form.

In another embodiment, the PDE1 inhibitors for use in the methods of treatment and prophylaxis described herein are Compound of Formula I, e.g. Formula I-A and I-B:

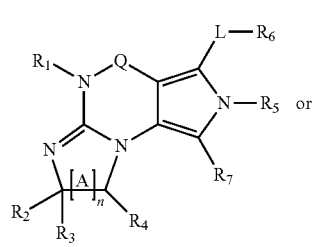

Formula I-A or

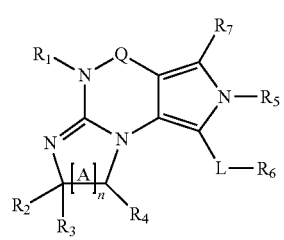

Formula I-B wherein
(i) Q is C(=O), C(=S), C(=N($R_{20}$)) or CH$_2$;
(ii) L is a single bond, —N(H)—, —CH$_2$—, —S—, —S(O)— or —S(O$_2$)—;
(iii) $R_1$ is H or $C_{1-4}$ alkyl (e.g., methyl);
(iv) $R_4$ is H or $C_{1-6}$ alkyl (e.g., methyl or isopropyl) and $R_2$ and $R_3$ are, independently,
H or $C_{1-6}$alkyl (e.g., methyl, isopropyl) optionally substituted with halo or hydroxy (e.g., $R_2$ and $R_3$ are both methyl, or $R_2$ is H and $R_3$ is methyl, ethyl, isopropyl or hydroxyethyl), aryl,
heteroaryl,
(optionally hetero)arylalkoxy, or
(optionally hetero)aryl$C_{1-6}$alkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);

(v) $R_5$ is
a) -D-E-F, wherein:
D is $C_{1-4}$ alkylene (e.g., methylene, ethylene or prop-2-yn-1-ylene);
E is a single bond, $C_{2-4}$ alkynylene (e.g., —C≡C—), arylene (e.g., phenylene) or heteroarylene (e.g., pyridylene);
F is
H,
aryl (e.g., phenyl),
heteroaryl (e.g., pyridyl, diazolyl, triazolyl, for example, pyrid-2-yl, imidazol-1-yl, 1,2,4-triazol-1-yl),
halo (e.g., F, Br, Cl),
halo$C_{1-4}$alkyl (e.g., trifluoromethyl),
—C(O)—$R_{15}$,
—N($R_{16}$)($R_{17}$), or
$C_{3-7}$ cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
wherein D, E and F are independently and optionally substituted with one or more halo (e.g., F, Cl or Br), $C_{1-4}$ alkyl (e.g., methyl), halo$C_{1-4}$alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$ alkyl (e.g., 5-methylpyrid-2-yl), or F is aryl, e.g., phenyl, substituted with one or more halo (e.g., 4-fluorophenyl) or F is a $C_{3-7}$ heterocycloalkyl (e.g., pyrrolidinyl) optionally substituted with a $C_{1-6}$alkyl (e.g., 1-methylpyrrolidin-3-yl); or
b) a substituted heteroarylalkyl, e.g., substituted with haloalkyl;
c) attached to the nitrogen on the pyrrolo portion of Formula I-A or I-B and is a moiety of Formula A

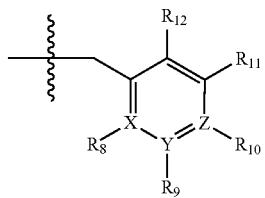

Formula A wherein X, Y and Z are, independently, N or C, and $R_8$, $R_9$, $R_{11}$ and $R_{12}$ are independently H or halogen (e.g., Cl or F), and $R_{10}$ is
halogen,
$C_{1-4}$ alkyl,
$C_{3-7}$ cycloalkyl,
$C_{1-4}$ haloalkyl (e.g., trifluoromethyl),
aryl (e.g., phenyl),
heteroaryl (e.g., pyridyl (for example pyrid-2-yl), or thiadiazolyl (e.g., 1,2,3-thiadiazol-4-yl)), diazolyl, triazolyl, tetrazolyl,
arylcarbonyl (e.g., benzoyl),
alkylsulfonyl (e.g., methylsulfonyl),
heteroarylcarbonyl, or
alkoxycarbonyl;
provided that when X, Y, or Z is nitrogen, $R_8$, $R_9$, or $R_{10}$, respectively, is not present;

(vi) $R_6$ is
H,
$C_{1-4}$ alkyl,
$C_{3-7}$ cycloalkyl (e.g., cyclopentyl),
aryl (e.g., phenyl),
heteroaryl (e.g., pyrid-4-yl),
aryl$C_{1-4}$alkyl (e.g., benzyl),
arylamino (e.g., phenylamino),
heteroarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$);
wherein the aryl or heteroaryl is optionally substituted with one or more halo (e.g., F, Cl), hydroxy or $C_{1-6}$ alkoxy;
(vii) $R_7$ is H, $C_{1-6}$alkyl, halogen (e.g., Cl), —N($R_{18}$)($R_{19}$);
(viii) n=0 or 1;
(ix) when n=1, A is —C($R_{13}R_{14}$)—, wherein $R_{13}$ and $R_{14}$, are, independently, H or $C_{1-4}$ alkyl, aryl, heteroaryl, (optionally hetero)aryl$C_{1-4}$alkoxy or (optionally hetero)aryl$C_{1-4}$alkyl;
(x) $R_{15}$ is $C_{1-4}$ alkyl, halo$C_{1-4}$alkyl, —OH or —O$C_{1-4}$alkyl (e.g., —OCH$_3$)
(xi) $R_{16}$ and $R_{17}$ are independently H or $C_{1-4}$ alkyl;
(xii) $R_{18}$ and $R_{19}$ are independently H, $C_{1-4}$alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
(xiii) $R_{20}$ is H, $C_{1-4}$ alkyl or $C_{3-7}$ cycloalkyl;
in free or salt form.
1.1 any of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 750 nM, more preferably less than 500 nM, more preferably less than 50 nM in an immobilized-metal affinity particle reagent PDE assay,
in free or salt form.

The invention further provides optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, in free or salt form, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., a Compound of Formula III:

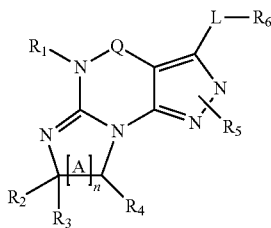

Formula III wherein
(xiv) Q is C(=S), C(=N($R_{20}$)) or $CH_2$;
(xv) L is a single bond, —N(H)—, —$CH_2$—;
(xvi) $R_1$ is H or $C_{1-4}$ alkyl (e.g., methyl or ethyl);
(xvii) $R_4$ is H or $C_{1-6}$ alkyl (e.g., methyl, isopropyl) and $R_2$ and $R_3$ are, independently:
  H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl),
  aryl,
  heteroaryl,
  (optionally hetero)arylalkoxy,
  (optionally hetero)aryl$C_{1-6}$alkyl, or
  $R_2$ and $R_3$ together form a 3- to 6-membered ring;
  or
  $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(xviii) $R_5$ is
  d) -D-E-F, wherein:
    D is $C_{1-4}$ alkylene (e.g., methylene, ethylene or prop-2-yn-1-ylene);
    E is a single bond, $C_{2-4}$ alkynylene (e.g., —C≡C—), arylene (e.g., phenylene) or heteroarylene (e.g., pyridylene);
    F is
      H,
      aryl (e.g., phenyl),
      heteroaryl (e.g., pyridyl, diazolyl, triazolyl, for example, pyrid-2-yl, imidazol-1-yl, 1,2,4-triazol-1-yl),
      halo (e.g., F, Br, Cl),
      halo$C_{1-4}$alkyl (e.g., trifluoromethyl),
      —C(O)—$R_{15}$,
      —N($R_{16}$)($R_{17}$),
      —S(O)$_2R_{21}$ or
      $C_{3-7}$ cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);
    wherein D, E and F are independently and optionally substituted with one or more:
      halo (e.g., F, Cl or Br),
      $C_{1-4}$ alkyl (e.g., methyl),
      halo$C_{1-4}$alkyl (e.g., trifluoromethyl),
      $C_{1-4}$ alkoxy) or
      $C_{1-4}$ alkyl (e.g., 5-methylpyrid-2-yl),
    for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl),
    or F is aryl, e.g., phenyl, substituted with one or more halo (e.g., 4-fluorophenyl)
    or F is a $C_{3-7}$ heterocycloalkyl (e.g., pyrrolidinyl) optionally substituted with a $C_{1-6}$alkyl (e.g., 1-methylpyrrolidin-3-yl);
    or
  e) a substituted heteroarylalkyl, e.g., substituted with haloalkyl;
  f) attached to one of the nitrogens on the pyrazolo portion of Formula III and is a moiety of Formula A

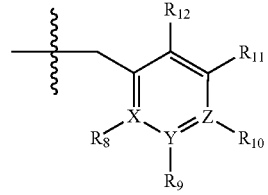

Formula A wherein X, Y and Z are, independently, N or C, and $R_8$, $R_9$, $R_{11}$ and $R_{12}$ are independently H or halogen (e.g., Cl or F), and $R_{10}$ is:
  halogen,
  $C_{1-4}$ alkyl,
  $C_{3-7}$ cycloalkyl,
  het$C_{3-7}$cycloalkyl (e.g., pyrrolidinyl or piperidinyl),
  $C_{1-4}$ haloalkyl (e.g., trifluoromethyl),
  aryl (e.g., phenyl),
  heteroaryl (e.g., pyridyl (for example pyrid-2-yl), or thiadiazolyl (e.g., 1,2,3-thiadiazol-4-yl)), diazolyl, triazolyl, tetrazolyl,
  arylcarbonyl (e.g., benzoyl),
  alkylsulfonyl (e.g., methylsulfonyl),
  heteroarylcarbonyl, or
  alkoxycarbonyl;
wherein the aryl, heteroaryl, cycloalkyl or heterocycloalkyl is independently and optionally substituted with one or more halo (e.g., F or Cl), $C_{1-4}$ alkyl, $C_{1-4}$ alkoxy, $C_{1-4}$ haloalkyl (e.g., trifluoromethyl), —SH;
preferably $R_{10}$ is phenyl, pyridyl, piperidinyl or pyrrolidinyl optionally substituted with the substituents previously defined, e.g. optionally substituted with halo or alkyl provided that when X, Y, or Z is nitrogen, $R_8$, $R_9$, or $R_{10}$, respectively, is not present;
(xix) $R_6$ is
  H,
  $C_{1-4}$ alkyl,
  $C_{3-7}$ cycloalkyl (e.g., cyclopentyl),
  aryl (e.g., phenyl),
  heteroaryl (e.g., pyridyl, for example, pyrid-4-yl),
  aryl$C_{1-4}$alkyl (e.g., benzyl),
  arylamino (e.g., phenylamino),
  heterarylamino,
  N,N-di$C_{1-4}$alkylamino,
  N,N-diarylamino,
  N-aryl-N-(aryl$C_{1-4}$alkyl)amino (e.g., N-phenyl-N-(1,1'-biphen-4-ylmethyl)amino), or
  —N($R_{18}$)($R_{19}$);

wherein the aryl or heteroaryl is optionally substituted with one or more halo (e.g., F, Cl), hydroxy, $C_{1-6}$ alkyl, $C_{1-6}$ alkoxy, $C_{3-8}$ cycloalkyl, for example, $R_6$ is 4-hydroxyphenyl or 4-fluorophenyl, (xx) n=0 or 1;

(xxi) when n=1, A is —$C(R_{13}R_{14})$—, wherein $R_{13}$ and $R_{14}$, are, independently, H or $C_{1-4}$ alkyl, aryl, heteroaryl, (optionally hetero)aryl$C_{1-4}$alkoxy(optionally hetero)aryl$C_{1-4}$alkyl or $R_{13}$ or $R_{14}$ can form a bridge with $R_2$ or $R_4$;

(xxii) $R_{15}$ is $C_{1-4}$ alkyl, halo$C_{1-4}$alkyl, —OH or —$OC_{1-4}$alkyl (e.g., —$OCH_3$)

(xxiii) $R_{16}$ and $R_{17}$ are independently H or $C_{1-4}$ alkyl;

(xxiv) $R_{18}$ and $R_{19}$ are independently

H, $C_{1-4}$ alky, $C_{3-8}$ cycloalkyl, hetero$C_{3-8}$cycloalkyl, aryl (e.g., phenyl), or heteroaryl, wherein said aryl or heteroaryl is optionally substituted with one or more halo (e.g., fluorophenyl, e.g., 4-fluorophenyl), hydroxy (e.g., hydroxyphenyl, e.g., 4-hydroxyphenyl or 2-hydroxyphenyl), $C_{1-6}$alkyl, halo$C_{1-6}$ alkyl, $C_{1-6}$ alkoxy, aryl, heteroaryl, or $C_{3-8}$ cycloalkyl;

(xxv) $R_{20}$ is H, $C_{1-4}$alkyl (e.g., methyl) or $C_{3-7}$cycloalkyl, (xxvi) $R_{21}$ is $C_{1-6}$ alkyl;

in free or salt form.

In yet another embodiment, the invention also provides a Compound of Formula IV:

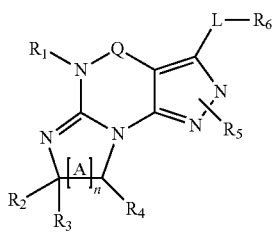

Formula IV wherein

Q is C(=S), C(=N($R_{20}$)) or $CH_2$;

L is a single bond, —N(H)—, —$CH_2$—;

$R_1$ is H or $C_{1-4}$ alkyl (e.g., methyl or ethyl);

$R_4$ is H or $C_{1-6}$ alkyl (e.g., methyl, isopropyl) and $R_2$ and $R_3$ are, independently, H or $C_{1-6}$alkyl (e.g., methyl or isopropyl) optionally substituted with halo or hydroxy (e.g., $R_2$ and $R_3$ are both methyl, or $R_2$ is H and $R_3$ is methyl, ethyl, isopropyl or hydroxyethyl), aryl, heteroaryl, (optionally hetero)arylalkoxy, or (optionally hetero)aryl$C_{1-6}$alkyl; or $R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);

$R_5$ is a) -D-E-F, wherein:

D is $C_{1-4}$ alkylene (e.g., methylene, ethylene or prop-2-yn-1-ylene);

E is a single bond, $C_{2-4}$ alkynylene (e.g., —C≡C—), arylene (e.g., phenylene) or heteroarylene (e.g., pyridylene);

F is H, aryl (e.g., phenyl), heteroaryl (e.g., pyridyl, diazolyl, triazolyl, for example, pyrid-2-yl, imidazol-1-yl, 1,2,4-triazol-1-yl), halo (e.g., F, Br, Cl), halo$C_{1-4}$alkyl (e.g., trifluoromethyl), —C(O)—$R_{15}$, —$N(R_{16})(R_{17})$, —$S(O)_2R_{21}$ or $C_{3-7}$ cycloalkyl optionally containing at least one atom selected from a group consisting of N or O (e.g., cyclopentyl, cyclohexyl, pyrrolidinyl (e.g., pyrrolidin-3-yl), tetrahydro-2H-pyran-4-yl, or morpholinyl);

wherein D, E and F are independently and optionally substituted with one or more:

halo (e.g., F, Cl or Br), $C_{1-4}$ alkyl (e.g., methyl), halo$C_{1-4}$alkyl (e.g., trifluoromethyl), for example, F is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-4}$alkyl (e.g., 5-trifluoromethylpyrid-2-yl) or $C_{1-4}$ alkyl (e.g., 5-methylpyrid-2-yl), or F is aryl, e.g., phenyl, substituted with one or more halo (e.g., 4-fluorophenyl)

or F is a $C_{3-7}$ heterocycloalkyl (e.g., pyrrolidinyl) optionally substituted with a $C_{1-6}$alkyl (e.g., 1-methylpyrrolidin-3-yl);

or b) a substituted heteroarylalkyl, e.g., substituted with haloalkyl;

c) attached to one of the nitrogens on the pyrazolo portion of Formula IV and is a moiety of Formula A

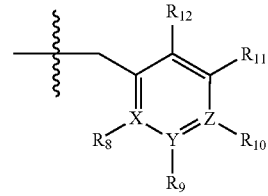

Formula A wherein X, Y and Z are, independently, N or C, and $R_8$, $R_9$, $R_{11}$ and $R_{12}$ are independently H or halogen (e.g., Cl or F), and $R_{10}$ is:

halogen, $C_{1-4}$ alkyl, $C_{3-7}$ cycloalkyl, $C_{1-4}$ haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl;

provided that when X, Y, or Z is nitrogen, $R_8$, $R_9$, or $R_{10}$, respectively, is not present;

$R_6$ is
H,
$C_{1-4}$ alkyl,
$C_{3-7}$ cycloalkyl (e.g., cyclopentyl),
aryl (e.g., phenyl),
heteroaryl (e.g., pyridyl, for example, pyrid-4-yl),
aryl$C_{1-4}$alkyl (e.g., benzyl),
arylamino (e.g., phenylamino),
heterarylamino,
N,N-di$C_{1-4}$alkylamino,
N,N-diarylamino,
N-aryl-N-(aryl$C_{1-4}$alkyl)amino (e.g., N-phenyl-N-(1,1'-biphen-4-ylmethyl)amino), or
—N($R_{18}$)($R_{19}$);
wherein the aryl or heteroaryl is optionally substituted with one or more halo (e.g., F, Cl), hydroxy or $C_{1-6}$ alkoxy, for example, $R_6$ is 4-hydroxyphenyl or 4-fluorophenyl,
n=0 or 1;
when n=1, A is —C($R_{13}R_{14}$)—, wherein $R_{13}$ and $R_{14}$, are, independently, H or $C_{1-4}$ alkyl, aryl, heteroaryl, (optionally hetero)aryl$C_{1-4}$alkoxy or (optionally hetero)aryl$C_{1-4}$alkyl;
$R_{15}$ is $C_{1-4}$ alkyl, halo$C_{1-4}$alkyl, —OH or —O$C_{1-4}$alkyl (e.g., —OCH$_3$)
$R_{16}$ and $R_{17}$ are independently H or $C_{1-4}$ alkyl;
$R_{18}$ and $R_{19}$ are independently H, $C_{1-4}$ alky or aryl (e.g., phenyl) wherein said aryl is optionally substituted with one or more halo (e.g., fluorophenyl, e.g., 4-fluorophenyl) or hydroxy (e.g., hydroxyphenyl, e.g., 4-hydroxyphenyl or 2-hydroxyphenyl)
$R_{20}$ is H, $C_{1-4}$ alkyl (e.g., methyl) or $C_{3-7}$ cycloalkyl,
$R_{21}$ is $C_{1-6}$ alkyl;
in free or salt form.

In still yet another embodiment, the invention provides that the PDE1 inhibitors for use in the methods of treatment and prophylaxis which are described herein may be selected from any of the following publications: US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 011/153136, and WO 2011/153138, the entire contents of each of which are incorporated herein by reference in their entireties.

In yet another embodiment the invention provides that the PDE1 inhibitors for use in the methods of treatment and prophylaxis described herein are compounds of Formula V:

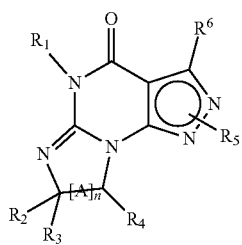

Formula V wherein
(i) $R_1$ is H or $C_{1-4}$ alkyl (e.g., methyl);
(ii) $R_4$ is H or $C_{1-4}$ alkyl and $R_2$ and $R_3$ are, independently, H or $C_{1-4}$ alkyl (e.g., $R_2$ and $R_3$ are both methyl, or $R_2$ is H and $R_3$ is isopropyl), aryl, heteroaryl, (optionally hetero)arylalkoxy, or (optionally hetero)arylalkyl;
or
$R_2$ is H and $R_3$ and $R_4$ together form a di-, tri- or tetramethylene bridge (pref. wherein the $R_3$ and $R_4$ together have the cis configuration, e.g., where the carbons carrying $R_3$ and $R_4$ have the R and S configurations, respectively);
(iii) $R_5$ is a substituted heteroarylalkyl, e.g., substituted with haloalkyl or
$R_5$ is attached to one of the nitrogens on the pyrazolo portion of Formula V and is a moiety of Formula A

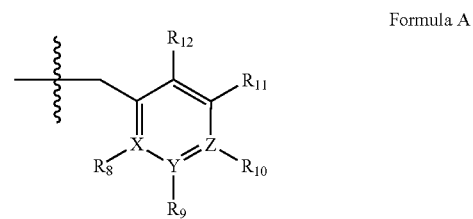

Formula A wherein X, Y and Z are, independently, N or C, and $R_8$, $R_9$, $R_{11}$ and $R_{12}$ are independently H or halogen (e.g., Cl or F), and $R_{10}$ is halogen, alkyl, cycloalkyl, haloalkyl (e.g., trifluoromethyl), aryl (e.g., phenyl), heteroaryl (e.g., pyridyl (for example pyrid-2-yl), or thiadiazolyl (e.g., 1,2,3-thiadiazol-4-yl)), diazolyl, triazolyl, tetrazolyl, arylcarbonyl (e.g., benzoyl), alkylsulfonyl (e.g., methylsulfonyl), heteroarylcarbonyl, or alkoxycarbonyl; provided that when X, Y, or Z is nitrogen, $R_8$, $R_9$, or $R_{10}$, respectively, is not present; and
(iv) $R_6$ is H, alkyl, aryl, heteroaryl, arylalkyl (e.g., benzyl), arylamino (e.g., phenylamino), heterarylamino, N,N-dialkylamino, N,N-diarylamino, or N-aryl-N-(arylakyl)amino (e.g., N-phenyl-N-(1,1'-biphen-4-ylmethyl)amino); and
(v) n=0 or 1;
(vi) when n=1, A is —C($R_{13}R_{14}$)—
wherein $R_{13}$ and $R_{14}$, are, independently, H or $C_{1-4}$ alkyl, aryl, heteroaryl, (optionally hetero)arylalkoxy or (optionally hetero)arylalkyl;

in free, salt or prodrug form, including its enantiomers, diastereoisomers and racemates.

In one embodiment the invention provides that the PDE1 inhibitors for use in the methods of treatment and prophylaxis described herein are compounds of Formula VI:

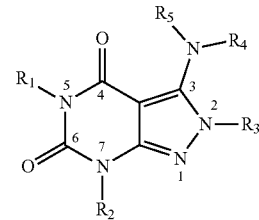

Formula VI wherein:
(i) $R_1$ is H or alkyl;
(ii) $R_2$ is H, alkyl, cycloalkyl, haloalkyl, alkylaminoalkyl, hydroxyalkyl, arylalkyl, heteroarylalkyl, or alkoxyarylalkyl;

(iii) R₃ is heteroarylmethyl or formula A

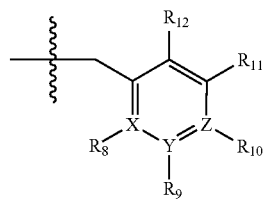

Formula A wherein X, Y and Z are, independently, N or C, and $R_8$, $R_9$, $R_{11}$ and $R_{12}$ are independently H or halogen; and $R_{10}$ is halogen, alkyl, cycloalkyl, haloalkyl, aryl, heteroaryl, alkyl sulfonyl, arylcarbonyl, heteroarylcarbonyl, alkoxycarbonyl, or aminocarbonyl;
(iv) R₄ is aryl or heteroaryl; and
(v) R₅ is H, alkyl, cycloalkyl, heteroaryl, aryl, p-benzylaryl;

provided that when X, Y or X is nitrogen, $R_8$, $R_9$ or $R_{10}$, respectively, is not present; wherein "alk" or "alkyl" refers to $C_{1-6}$ alkyl and "cycloalkyl" refers to $C_{3-6}$ cycloalkyl, in free, salt or physiologically hydrolysable and acceptable ester prodrug form.

In one embodiment the invention provides that the PDE1 inhibitors for use in the methods of treatment and prophylaxis described herein are compounds of Formula VII:

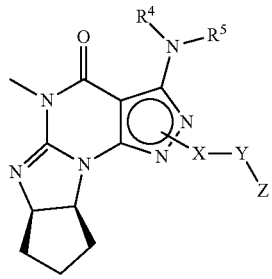

Formula VII (i) X is $C_{1-6}$ alkylene (e.g., methylene, ethylene or prop-2-yn-1-ylene);
(ii) Y is a single bond, alkynylene (e.g., —C≡C—), arylene (e.g., phenylene) or heteroarylene (e.g., pyridylene);
(iii) Z is H, aryl (e.g., phenyl), heteroaryl (e.g., pyridyl, e.g., pyrid-2-yl), halo (e.g., F, Br, Cl), halo$C_{1-6}$alkyl (e.g., trifluoromethyl), —C(O)—R¹, —N(R²)(R³), or $C_{3-7}$ cycloalkyl optionally containing at least one atom selected from a group consisting of N or O (e.g., cyclopentyl, cyclohexyl, tetrahydro-2H-pyran-4-yl, or morpholinyl);
(iv) R¹ is $C_{1-6}$alkyl, halo$C_{1-6}$alkyl, —OH or —O$C_{1-6}$alkyl (e.g., —OCH₃);
(v) R² and R³ are independently H or $C_{1-6}$alkyl;
(vi) R⁴ and R⁵ are independently H, $C_{1-6}$ alky or aryl (e.g., phenyl) optionally substituted with one or more halo (e.g., fluorophenyl, e.g., 4-fluorophenyl), hydroxy (e.g., hydroxyphenyl, e.g., 4-hydroxyphenyl or 2-hydroxyphenyl) or $C_{1-6}$ alkoxy;
(vii) wherein X, Y and Z are independently and optionally substituted with one or more halo (e.g., F, Cl or Br), $C_{1-6}$alkyl (e.g., methyl), halo$C_{1-6}$alkyl (e.g., trifluoromethyl), for example, Z is heteroaryl, e.g., pyridyl substituted with one or more halo (e.g., 6-fluoropyrid-2-yl, 5-fluoropyrid-2-yl, 6-fluoropyrid-2-yl, 3-fluoropyrid-2-yl, 4-fluoropyrid-2-yl, 4,6-dichloropyrid-2-yl), halo$C_{1-6}$alkyl (e.g., 5-trifluoromethylpyrid-2-yl) or $C_{1-6}$-alkyl (e.g., 5-methylpyrid-2-yl), or Z is aryl, e.g., phenyl, substituted with one or more halo (e.g., 4-fluorophenyl), in free, salt or prodrug form.

In one embodiment the invention provides that the PDE1 inhibitors for use in the methods of treatment and prophylaxis described herein are compounds of Formula VIII:

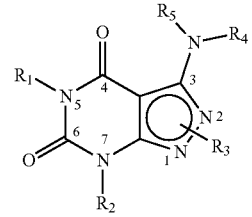

Formula VIII wherein
(i) R₁ is H or $C_{1-6}$alkyl;
(ii) R₂ is
H,
$C_{1-6}$ alkyl,
$C_{3-8}$ cycloalkyl optionally substituted with one or more amino,
$C_{3-8}$ heterocycloalkyl optionally substituted with $C_{1-6}$ alkyl,
$C_{3-8}$ cycloalkyl-$C_{1-6}$ alkyl,
$C_{1-6}$ haloalkyl,
$C_{0-6}$ alkylamino$C_{0-6}$ alkyl,
hydroxy$C_{1-6}$alkyl,
aryl$C_{0-6}$alkyl,
heteroarylalkyl,
$C_{1-6}$alkoxyaryl$C_{1-6}$alkyl, or
G-J wherein:
G is a single bond or, alkylene;
J is cycloalkyl or heterocycloalkyl optionally substituted with alkyl;
(iii) R₃ is
a) -D-E-F wherein
1. D is single bond, $C_{1-6}$ alkylene or aryl$C_{1-6}$alkylene;
2. E is a $C_{1-6}$ alkylene, arylene, $C_{1-6}$ alkylarylene, amino$C_{1-6}$alkylene- or amino; and
3. F is hetero$C_{3-8}$cycloalkyl optionally substituted with $C_{1-6}$alkyl;
(iv) R₄ is aryl optionally substituted with one or more halo, hydroxy or $C_{1-6}$alkoxy; heteroaryl; or heteroC₃₋₆cycloalkyl; and
(v) R₅ is H, $C_{1-6}$ alkyl, $C_{3-8}$ cycloalkyl, heteroaryl, aryl or p-benzylaryl;

wherein "alk", "alkyl", "haloalkyl" or "alkoxy" refers to $C_{1-6}$ alkyl and "cycloalkyl" refers to $C_{3-8}$ cycloalkyl;
in free or salt form.

In one embodiment the invention provides that the PDE1 inhibitors for use in the methods of treatment and prophylaxis described herein are compounds of Formula IX:

Formula IX wherein
(i) Q is —C(=S)—, —C(=N($R_6$))— or —C($R_{14}$)($R_{15}$)—;
(ii) $R_1$ is H or $C_{1-6}$alkyl (e.g., methyl or ethyl);
(iii) $R_2$ is
   H,
   $C_{1-6}$alkyl (e.g., isopropyl, isobutyl, 2-methylbutyl or 2,2-dimethylpropyl) wherein said alkyl group is optionally substituted with one or more halo (e.g., fluoro) or hydroxy (e.g., hydroxy$C_{1-6}$alkyl, for example 1-hydroxyprop-2-yl or 3-hydroxy-2-methylpropyl),
   halo$C_{1-6}$alkyl (e.g., trifluoromethyl or 2,2,2-trifluoroethyl), N($R_{14}$)($R_{15}$)—$C_{1-6}$alkyl (e.g., 2-(dimethylamino)ethyl or 2-aminopropyl),
   aryl$C_{0-6}$alkyl (e.g., phenyl or benzyl), wherein said aryl is optionally substituted with one or more $C_{1-6}$alkoxy, for example, $C_{1-6}$alkoxyaryl$C_{0-6}$alkyl (e.g., 4-methoxybenzyl),
   heteroaryl$C_{0-6}$alkyl (e.g., pyridinylmethyl), wherein said heteroaryl is optionally substituted with one or more $C_{1-6}$alkoxy (e.g., $C_{1-6}$alkoxyheteroaryl$C_{1-6}$alkyl);
   -G-J wherein G is a single bond or $C_{1-6}$ alkylene (e.g., methylene) and J is $C_{3-8}$ cycloalkyl or hetero$C_{3-8}$-cycloalkyl (e.g., oxetan-2-yl, pyrrolidin-3-yl, pyrrolidin-2-yl) wherein the cycloalkyl and heterocycloalkyl group are optionally substituted with one or more $C_{1-6}$ alkyl or amino, for example,
      —$C_{0-4}$alkyl-$C_{3-8}$cycloalkyl (e.g., —$C_{0-4}$alkyl-cyclopentyl, —$C_{0-4}$alkyl-cyclohexyl or —$C_{0-4}$alkyl-cyclopropyl), wherein said cycloalkyl is optionally substituted with one or more $C_{1-6}$alkyl or amino (for example, 2-aminocyclopentyl or 2-aminocyclohexyl),
      —$C_{0-4}$alkyl-$C_{3-8}$heterocycloalkyl (e.g., —$C_{0-4}$alkyl-pyrrolidinyl, for example, —$C_{0-4}$alkylpyrrolidin-3-yl) wherein said heterocycloalkyl is optionally substituted with $C_{1-6}$alkyl (e.g., methyl), for example, 1-methylpyrrolidin-3-yl, 1-methyl-pyrrolindin-2-yl, 1-methyl-pyrrolindin-2-yl-methyl or 1-methyl-pyrrolindin-3-yl-methyl);
(iv) $R_3$ is
   1) -D-E-F wherein:
      D is a single bond, $C_{1-6}$ alkylene (e.g., methylene), or aryl$C_{1-6}$alkylene (e.g., benzylene or —$CH_2C_6H_4$—);
      E is
         a single bond,
         $C_{1-4}$ alkylene (e.g., methylene, ethynylene, prop-2-yn-1-ylene),
         $C_{0-4}$ alkylarylene (e.g., phenylene or —$C_6H_4$—, -benzylene- or —$CH_2C_6H_4$—), wherein the arylene group is optionally substituted with halo (e.g., Cl or F),
         heteroarylene (e.g., pyridinylene or pyrimidinylene),
         amino$C_{1-6}$alkylene (e.g., —$CH_2$N(H)—),
         amino (e.g., —N(H)—);
         $C_{3-8}$ cycloalkylene optionally containing one or more heteroatom selected from N or O (e.g., piperidinylene),
      F is
         H,
         halo (e.g., F, Br, Cl),
         $C_{1-6}$alkyl (e.g., isopropyl or isobutyl),
         halo$C_{1-6}$alkyl (e.g., trifluoromethyl),
         aryl (e.g., phenyl),
         $C_{3-8}$cycloalkyl optionally containing one or more atom selected from a group consisting of N, S or O (e.g., cyclopentyl, cyclohexyl, piperidinyl, pyrrolidinyl, tetrahydro-2H-pyran-4-yl, or morpholinyl), and optionally substituted with one or more $C_{1-6}$alkyl (e.g., methyl or isopropyl), for example, 1-methylpyrrolidin-2-yl, pyrrolidin-1-yl, pyrrolidin-2-yl, piperidin-2-yl, 1-methylpiperidin-2-yl, 1-ethylpiperidin-2-yl,
         heteroaryl (e.g., pyridyl (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl)), triazolyl (e.g., 1,2,4-triazol-1-yl), tetrazolyl (e.g., tetrazol-5-yl), alkyloxadiazolyl (e.g., 5-methyl-1,2,4-oxadiazol), wherein said heteroaryl is optionally substituted with one or more $C_{1-6}$alkyl, halo (e.g., fluoro) or halo$C_{1-6}$alkyl;
         $C_{1-6}$ alkoxy,
         —O-halo$C_{1-6}$alkyl (e.g., —O—$CF_3$),
         $C_{1-6}$ alkylsulfonyl (for example, methylsulfonyl or —S(O)$_2$CH$_3$),
         —C(O)—$R_{13}$, wherein $R_{13}$ is —N($R_{14}$)($R_{15}$), $C_{1-6}$alkyl (e.g., methyl), —O$C_{1-6}$alkyl (e.g., —OCH$_3$), halo$C_{1-6}$alkyl (trifluoromethyl), aryl (e.g., phenyl), or heteroaryl;
         —N($R_{14}$)($R_{15}$);
      or
   2) a substituted heteroaryl$C_{1-6}$alkyl, e.g., substituted with halo$C_{1-6}$alkyl;
   or
   3) attached to one of the nitrogens on the pyrazolo portion of Formula I and is a moiety of Formula A Formula A wherein:
X, Y and Z are, independently, N or C,
$R_8$, $R_9$, $R_{11}$ and $R_{12}$ are independently H or halogen (e.g., Cl or F); and $R_{10}$ is
halogen (e.g., fluoro or chloro),
$C_{1-6}$alkyl,
$C_{3-8}$cycloalkyl,
hetero$C_{3-8}$cycloalkyl (e.g., pyrrolidinyl or piperidinyl),
halo$C_{1-6}$alkyl (e.g., trifluoromethyl),
aryl (e.g., phenyl) or heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkyloxadiazolyl (e.g., 5-methyl-1,2,4-oxadiazol), pyrazolyl (e.g., pyrazol-1-yl),
wherein said aryl, heteroaryl, cycloalkyl or heterocycloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl),
$C_{1-6}$alkyl sulfonyl (e.g., methyl sulfonyl), arylcarbonyl (e.g., benzoyl), heteroarylcarbonyl, $C_{1-6}$alkoxycarbonyl, (e.g., methoxycarbonyl), Aminocarbonyl,
—$N(R_{14})(R_{15})$;
preferably $R_{10}$ is phenyl, pyridyl, piperidinyl or pyrrolidinyl optionally substituted with the substituents previously defined, e.g. optionally substituted with halo or alkyl;
provided that when X, Y or X is nitrogen, $R_8$, $R_9$ or $R_{10}$, respectively, is not present;

(v) $R_4$ and $R_5$ are independently:
H,
$C_{1-6}$alkyl (e.g., methyl, isopropyl, isobutyl, n-propyl),
$C_{3-8}$cycloalkyl (e.g., cyclopentyl or cyclohexyl),
$C_{3-8}$heterocycloalkyl (e.g., pyrrolidinyl (for example pyrrolidin-3-yl or pyrrolidin-1-yl), piperidinyl (for example, piperidin-1-yl), morpholinyl),
—$C_{0-6}$alkylaryl (e.g., phenyl or benzyl) or
—$C_{0-6}$alkylheteroaryl (e.g., pyrid-4-yl, pyrid-2-yl or pyrazol-3-yl)
wherein said aryl or heteroaryl is optionally substituted with one or more halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl);
(vi) $R_6$ is H, $C_{1-6}$alkyl (e.g., methyl or ethyl) or $C_{3-8}$cycloalkyl;
(vii) $R_{14}$ and $R_{15}$ are independently H or $C_{1-6}$alkyl,
in free or salt form.

In one embodiment the invention provides that the PDE1 inhibitors for use in the methods of treatment and prophylaxis described herein are Formula X, selected from Formula X-A or X-B:

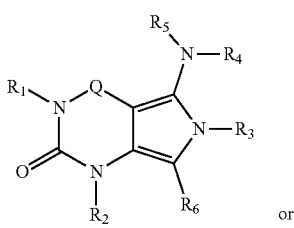

Formula X-A

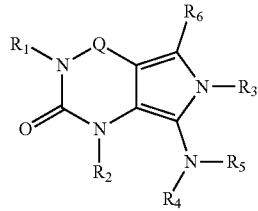

Formula X-B wherein
(i) Q is —C(=S)—, —C(=O)—, —C(=N(R_7))— or —C(R_{14})(R_{15})—;
(ii) $R_1$ is H or $C_{1-6}$alkyl (e.g., methyl or ethyl);
(iii) $R_2$ is H, $C_{1-6}$alkyl (e.g., isopropyl, isobutyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), for example, $R_2$ may be a trifluoromethyl or 2,2,2-trifluoroethyl, $N(R_{14})(R_{15})$—$C_{1-6}$alkyl (e.g., 2-(dimethylamino)ethyl or 2-aminopropyl), aryl$C_{1-6}$alkyl (e.g., phenyl or benzyl), heteroaryl $C_{1-6}$alkyl (e.g., pyridinylmethyl), $C_{1-6}$alkoxyaryl-$C_{1-6}$alkyl (e.g., 4-methoxybenzyl); -G-J wherein:
G is a single bond or, alkylene (e.g., methylene); J is cycloalkyl or heterocycloalkyl (e.g., oxetan-2-yl, pyrolyin-3-yl, pyrolyin-2-yl) optionally substituted with one or more $C_{1-6}$alkyl (e.g., (1-methylpyrolidin-2-yl)), amino (e.g., —$NH_2$), for example, -G-J may be —$C_{0-4}$alkyl-$C_{3-8}$cycloalkyl (e.g., cyclopentyl, cyclohexyl or cyclopropylmethyl) optionally substituted with one or more $C_{1-6}$alkyl, amino (e.g., —$NH_2$), for example, 2-aminocyclopentyl or 2-aminocyclohexyl, wherein said cycloalkyl optionally contains one or more heteroatom selected from N and O (e.g., pyrrolidinyl, for example, pyrrolidin-3-yl or pyrrolidin-2-yl, 1-methyl-pyrrolindin-2-yl, 1-methyl-pyrrolindin-3-yl, 1-methyl-pyrrolindin-2-yl-methyl or 1-methyl-pyrrolindin-3-yl-methyl);
(iv) $R_3$ is
1) -D-E-F wherein:
D is a single bond, $C_{i-6}$alkylene (e.g., methylene), or arylalkylene
(e.g., p-benzylene or —$CH_2C_6H_4$—);
E is a single bond,
$C_{1-6}$alkylene (e.g., methylene) $C_{2-6}$alkynylene (e.g., ethynylene, prop-2-yn-1-ylene), ethynylene, prop-2-yn-1-ylene), —$C_{0-4}$alkylarylene (e.g., phenylene or —$C_6H_4$—, -benzyleηε- or —$CH_2C_6H_4$—), wherein the arylene group is optionally substituted with halo (e.g., Cl or F), heteroarylene (e.g., pyridinylene or pyrimidinylene), amino$C_{i-6}$alkylene (e.g., —$CH_2N(H)$—), amino (e.g., —$N(H)$—);
$C_{3-8}$cycloalkylene optionally containing one or more heteroatom selected from N or O (e.g., piperidinylene),
F is
H,
halo (e.g., F, Br, Cl), $C_{1-6}$alkyl (e.g., isopropyl or isobutyl), halo$C_{1-6}$alkyl
(e.g., trifluoromethyl),
aryl (e.g., phenyl),
$C_{3-8}$cycloalkyl optionally containing at least one atom selected from a group consisting of N or O (e.g., cyclopentyl, N cyclohexyl, piperidinyl, pyrrolidinyl, tetrahydro-2H-pyran-4-yl, or morpholinyl), said cycloalkyl is optionally substituted with $C_{1-6}$alkyl (e.g., methyl or isopropyl), for example, 1-methylpyrrolidin-2-yl, pyrrolidin-1-yl, pyrrolidin-2-yl, piperidin-2-yl, 1-methyrpiperidin-2-yl, 1-ethylpiperidin-2-yl, heteroaryl optionally substituted with $C_{1-6}$alkyl, (e.g., pyridyl, (for example, pyrid-2-yl), pyrimidinyl (for example, pyrimidin-2-yl), thiadiazolyl (for example, 1,2,3-thiadiazol-4-yl), diazolyl (e.g., pyrazolyl (for example, pyrazol-1-yl) or imidazolyl (for example, imidazol-1-yl, 4-methylimidazolyl, 1-methylimidazol-2-yl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), wherein said heteroaryl is optionally substituted with halo (e.g., fluoro) or halo$Ci_{-6}$alkyl, for example, 6-fluoropyrid-2-yl; amino (e.g., —$NH_2$), $C_{1-6}$alkoxy, —O-halo$C_{1-6}$ alkyl (e.g., —O—$CF_3$), $C_{1-6}$alkylsulfonyl (for example, methylsulfonyl or —$S(O)_2CH_3$), —C(O)—$R_{13}$, —$N(R_{14})(R_{15})$; or 2) a substituted heteroarylaklyl, e.g., substituted with haloalkyl; or
3) attached to the nitrogen on the pyrrolo portion of Formula I and is a moiety of Formula A

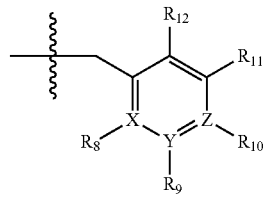

Formula A wherein X, Y and Z are, independently, N or C, and $R_8$, $R_9$, $R_{11}$ and $R_{12}$ are independently H or halogen (e.g., Cl or F); and $R_{10}$ is halogen, $C_{1-6}$alkyl, $C_{1-6}$alkoxy (e.g., methoxy), $C_{3-8}$cycloalkyl, hetero$C_{3-8}$cycloalkyl (e.g., pyrrolidinyl) halo$C_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl (e.g., imidazolyl or pyrazolyl), triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), $C_{1-6}$alkyl sulfonyl (e.g., methyl sulfonyl), arylcarbonyl (e.g., benzoyl), heteroarylcarbonyl, alkoxycarbonyl, (e.g., methoxycarbonyl), aminocarbonyl; wherein the aryl, heteroaryl, cycloalkyl or heterocycloalkyl is optionally substituted with one or more $C_{1-6}$alkyl (e.g., methyl), halogen (e.g., chloro or fluoro), halo$C_{1-6}$alkyl (e.g., trifluoromethyl), hydroxy, carboxy, —SH, or an additional aryl or heteroaryl (e.g., biphenyl or pyridylphenyl) preferably $R_{10}$ is phenyl or pyridyl, e.g., 2-pyridyl optionally substituted with the substituents previously defined;

provided that when X, Y or X is nitrogen, $R_8$, $R_9$ or $R_{10}$, respectively, is not present; (v) $R_4$ and $R_5$ are independently H, $Ci_{-6}$alkyl (e.g., methyl, isopropyl), $C_{3-8}$cycloalkyl (e.g., cyclopentyl), $C_{3-8}$heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl);

(vi) $R_6$ is H, $C_{1-6}$alkyl (e.g., methyl), hydroxy, $Ci_{-6}$alkoxy, aryloxy, —$N(R_{16})(R_{17})$, oxo (e.g., =O), or $C_{3-8}$Cycloalkyl;

(vii) $R_7$ is H, $C_{1-6}$alkyl (e.g., methyl) or $C_{3-8}$cycloalkyl wherein said cycloalkyl is optionally substituted with one or more oxo (e.g., 2,5-dioxopyrrolidin-1-yl);

(viii) $R_{13}$ is —$N(R_{14})(R_{15})$, $C_{1-6}$alkyl (e.g., methyl), —$OC_{1-6}$alkyl (e.g., —$OCH_3$), halo$C_{1-6}$alkyl (trifluoromethyl), aryl (e.g., phenyl), or heteroaryl; and (ix) $R_{14}$ and $R_{15}$ are independently H or $C_{1-6}$alkyl;

(x) $R_{16}$ and $R_{17}$ are independently H, $C_{1-6}$alkyl, aryl (e.g., phenyl), heteroaryl, wherein said aryl or heteroaryl is optionally substituted with halo (e.g., fluoro), $C_{1-6}$alkoxy (e.g., methoxy); in free or salt form.

In one embodiment the invention provides that the PDE1 inhibitors for use in the methods of treatment and prophylaxis described herein are Formula XI:

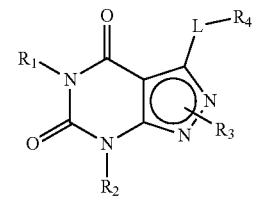

Formula XI wherein
(i) L is S, SO or $SO_2$;
(ii) $R_2$ is H or $C_{1-6}$alkyl (e.g., methyl or ethyl);
(iii) $R_2$ is
H,
$C_{1-6}$alkyl (e.g., isopropyl, isobutyl, neopentyl, 2-methylbutyl, 2,2-dimethylpropyl) wherein said alkyl group is optionally substituted with halo (e.g., fluoro) or hydroxy (e.g., 1-hydroxypropan-2-yl, 3-hydroxy-2-methylpropyl), —$C_{0-4}$alkyl-$C_{3-8}$cycloalkyl (e.g., cyclopentyl, cyclohexyl) optionally substituted with one or more amino (e.g., —$NH_2$), for example, 2-aminocyclopentyl or 2-aminocyclohexyl), wherein said cycloalkyl optionally contains one or more heteroatom selected from N and O and is optionally substituted with $C_{1-6}$alkyl (e.g., 1-methyl-pyrrolindin-2-yl, 1-methyl-pyrrolindin-3-yl, 1-methyl-pyrrolindin-2-yl-methyl or 1-methyl-pyrrolindin-3-yl-methyl), $C_{3-8}$heterocycloalkyl (e.g., pyrrolidinyl, for example, pyrrolidin-3-yl) optionally substituted with $C_{1-6}$alkyl (e.g., methyl), for example, 1-methylpyrrolidin-3-yl, $C_{3-8}$cycloalkyl-$C_{1-6}$alkyl (e.g., cyclopropylmethyl), halo$C_{1-6}$alkyl (e.g., trifluoromethyl, 2,2,2-trifluoroethyl), —$N(R_{14})(R_{15})$—$C_{1-6}$alkyl (e.g., 2-(dimethylamino)ethyl, 2-aminopropyl), hydroxy$C_{1-6}$alkyl (e.g., (e.g., 3-hydroxy-2-methylpropyl, 1-hydroxyprop-2-yl), aryl$C_{0-6}$alkyl (e.g., benzyl), heteroaryl$C_{1-6}$alkyl (e.g., pyridinylmethyl), $C_{1-6}$alkoxyaryl$C_{1-6}$alkyl (e.g., 4-methoxybenzyl); -G-J wherein: G is a single bond or, alkylene (e.g., methylene);

J is cycloalkyl or heterocycloalkyl (e.g., oxetan-2-yl, pyrolyin-3-yl, pyrolyin-2-yl) optionally substituted with $C_{1-6}$alkyl (e.g., (1-methylpyrolidin-2-yl));

(iv) $R_3$ is attached to one of the nitrogens on the pyrazolo portion of Formula I and is a moiety of Formula A

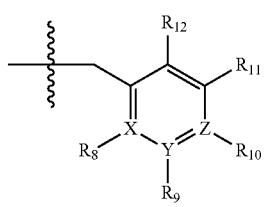

Formula A wherein X, Y and Z are, independently, N or C, and $R_8$, $R_9$, $R_{11}$ and $R_{12}$ are independently H or halogen (e.g., Cl or F); and $R_{10}$ is halogen, $C_{1-6}$alkyl, $C_{3-8}$cycloalkyl, heteroC$_{3-8}$-cycloalkyl (e.g., pyrrolidinyl or piperidinyl) haloC$_{1-6}$alkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-15 yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-i-yi), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl, pyridyl, e.g., 2-pyridyl, piperidinyl, or pyrrolidinyl; wherein the aryl, heteroaryl cycloalkyl or heterocycloalkyl is optionally substituted with one or more halo (e.g., F or Cl), $C_{1-6}$alkly, $C_{1-6}$alkoxy, $C_{1-4}$haloalkyl (e.g., trifluoromethyl), and/or —SH, provided that when X, Y or X is nitrogen, $R_8$, $R_9$ or $R_{10}$, respectively, is not present;

(v) $R_4$ is
H, $C_{1-6}$alkyl (e.g., methyl, isopropyl), $C_{3-8}$cycloalkyl (e.g., cyclopentyl), $C_{3-8}$heterocycloalkyl (e.g., pyrrolidin-3-yl), aryl (e.g., phenyl) or heteroaryl (e.g., pyrid-4-yl, pyrid-2-yl or pyrazol-3-yl) wherein said aryl or heteroaryl is optionally substituted with halo (e.g., 4-fluorophenyl), hydroxy (e.g., 4-hydroxyphenyl), $C_{1-6}$alkyl, $C_{1-6}$alkoxy or another aryl group (e.g., biphenyl-4-ylmethyl); (vi) $R_{14}$ and $R_{15}$ are independently H or $C_{1-6}$alkyl, in free or salt form.

In yet another embodiment the invention provides that the PDE1 inhibitors for use in the methods of treatment and prophylaxis described herein are Formula XII:

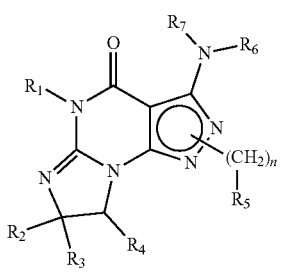

Formula XII wherein
(i) R 1 is H or C 1-4 alkyl (e.g., methyl or ethyl);
(ii) R 2 and R 3 are independently H or C 1-6 alkyl (e.g., methyl or ethyl);
(iii) R 4 is H or C 1-4 alkyl (e.g., methyl or ethyl);
(iv) R 5 is aryl (e.g., phenyl) optionally substituted with one or more groups independently selected from —C(=O)—C 1-6 alkyl (e.g., —C(=O)—CH 3) and C 1-6-hydroxyalkyl (e.g., 1-hydroxyethyl);
(v) R 6 and R 7 are independently H or aryl (e.g., phenyl) optionally substituted with one or more groups independently selected from C 1-6 alkyl (e.g., methyl or ethyl) and halogen (e.g., F or Cl), for example unsubstituted phenyl or phenyl substituted with one or more halogen (e.g., F) or phenyl substituted with one or more C 1-6 alkyl and one or more halogen or phenyl substituted with one C 1-6 alkyl and one halogen, for example 4-fluorophenyl or 3,4-difluorophenyl or 4-fluoro-3-methylphenyl;

and (vi) n is 1, 2, 3, or 4, in free or salt form.

The invention further provides the use of PDE1 inhibitors of any of the preceding formulae (e.g., Formula I, II, III, IV, V, VI, VII, VIII, IX, X, XI, XII), wherein the compound is selected from any of the following:

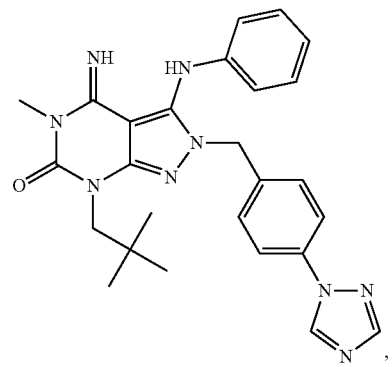

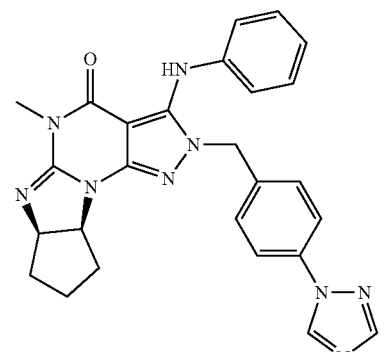

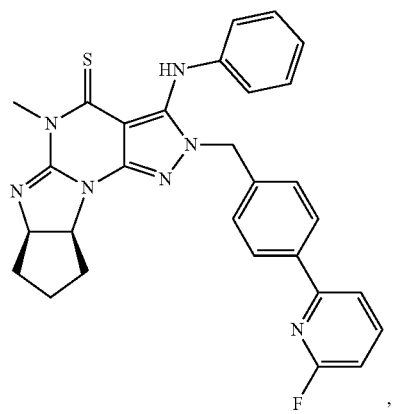

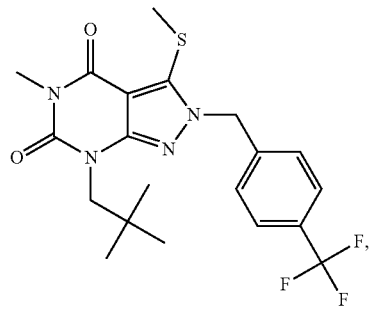
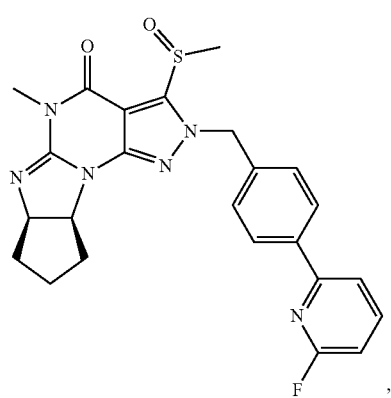
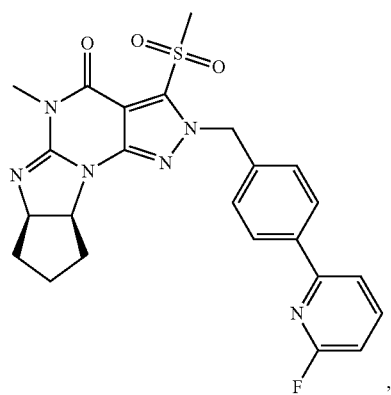
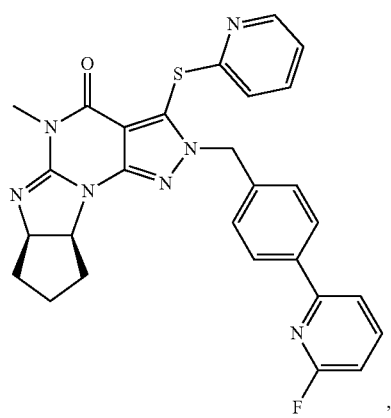
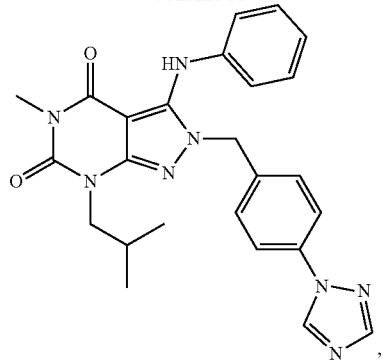
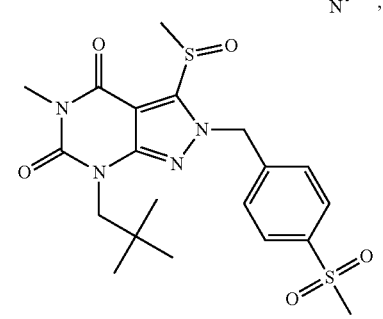
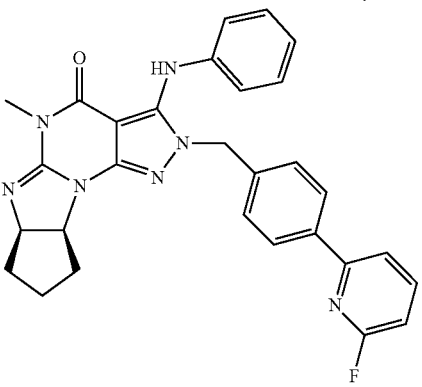
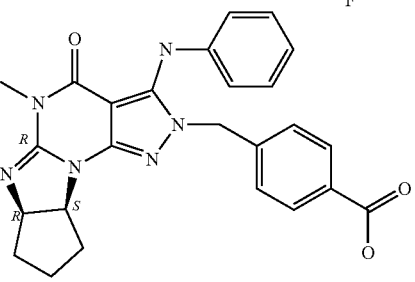
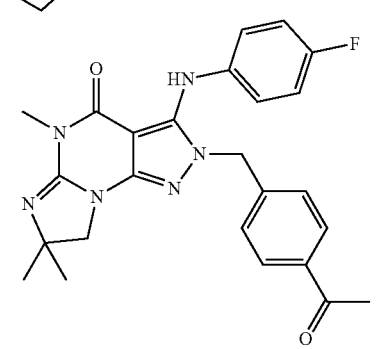
In one embodiment the invention provides administration of a PDE1 inhibitor for treatment or prophylaxis of inflammation or an inflammatory related disease or disorder, wherein the inhibitor is a compound according to the following:

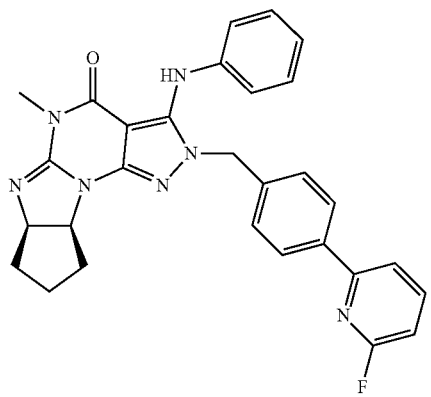

In still another embodiment, the invention provides administration of a PDE1 inhibitor for treatment or prophylaxis of inflammation or an inflammatory related disease or disorder, wherein the inhibitor is a compound according to the following:

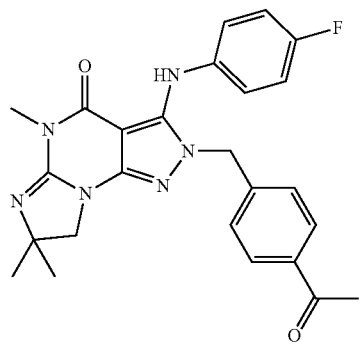 [SMILES: CC(=O)c1ccc(Cn2nc3c(c2Nc2ccc(F)cc2)C(=O)N(C)C2=NC(C)(C)CN23)cc1]

In one embodiment, selective PDE1 inhibitors of the any of the preceding formulae (e.g., Formula I, II, III, IV, V, VI, VII, VIII, IX, X, XI, XII) are compounds that inhibit phosphodiesterase-mediated (e.g., PDE1-mediated, especially PDE1B-mediated) hydrolysis of cGMP, e.g., the preferred compounds have an $IC_{50}$ of less than 1 μM, preferably less than 500 nM, preferably less than 50 nM, and preferably less than 5 nM in an immobilized-metal affinity particle reagent PDE assay, in free or salt form.

If not otherwise specified or clear from context, the following terms herein have the following meanings:

"Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

"Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Wherein the cycloalkyl optionally contains one or more atoms selected from N and O and/or S, said cycloalkyl may also be a heterocycloalkyl.

"Heterocycloalkyl" is, unless otherwise indicated, saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

"Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

"Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

For ease of reference, the atoms on the pyrazolo-pyrimidine core of the Compounds of the Invention are numbered in accordance with the numbering depicted in below for Formula I, unless otherwise noted or evident from the context.

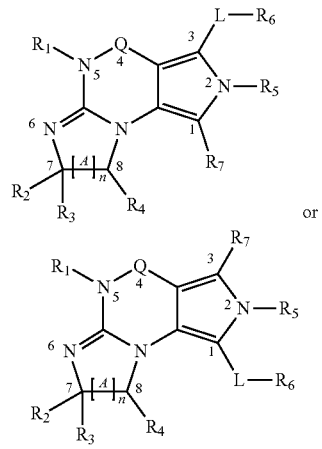

When E is phenylene, the numbering is as follows:

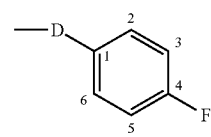

It is intended that wherein the substituents end in "ene", for example, alkylene, phenylene or arylalkylene, said substitutents are intended to bridge or be connected to two other substituents. Therefore, methylene is intended to be —$CH_2$— and phenylene intended to be —$C_6H_4$— and arylalkylene is intended to be —$C_6H_4$—$CH_2$— or —$CH_2$—$C_6H_4$—.

Compounds of the Invention, e.g., substituted 4,5,7,8-tetrahydro-2H-imidazo[1,2-a]pyrrolo[3,4-e]pyrimidine or 4,5,7,8,9-pentahydro-2H-pyrimido[1,2-a]pyrrolo[3,4-e]pyrimidine, e.g., Compounds of Formula I (Formula I-A and I-B), or a Compound of Formula II (e.g., II-A or II-B), may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention, encompassing any of the compounds disclosed herein, e.g., optionally substituted 4,5,7,8-tetrahydro-(optionally 4-thioxo or 4-imino)-(1H or 2H)-imidazo[1,2-a]pyrazolo[4,3-e]pyrimidine or 4,5,7,8,9-pentahydro-(1H or 2H)-pyrimido[1,2-a]pyrazolo[4,3-e]pyrimidine compounds, e.g., (1 or 2 and/or 3 and/or 5)-substituted 4,5,7,8-tetrahydro-1H-imidazo[1,2-a]pyrazolo[4,3-e]pyrimidine, 4,5,7,8-tetrahydro-2H-imidazo[1,2-a]pyrazolo[4,3-e]pyrimidine, 4,5,7,8-tetrahydro-(1H or 2H)-pyrimido[1,2-a]pyrazolo[4,3-e]pyrimidine-4(5H)-imine, 7,8-dihydro-1H-imidazo[1,2-a]pyrazolo[4,3-e]pyrimidine-4(5H)-thione or 7,8-dihydro-2H-imidazo[1,2-a]pyrazolo[4,3-e]pyrimidine-4(5H)-thione compounds, e.g., Compounds of Formula III, or Compound of Formula IV as described herein, may exist in free or salt form, e.g., as acid addition salts.

Compounds of the Invention may in some cases also exist in prodrug form. A prodrug form is compound which converts in the body to a Compound of the Invention. For example. when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and HO—$C_{1-4}$alkyl. As will be appreciated the term thus embraces conventional pharmaceutical prodrug forms.

In another embodiment, the invention further provides a pharmaceutical composition comprising a Compound of the Invention, in free, pharmaceutically acceptable salt or prodrug form, in admixture with a pharmaceutically acceptable carrier, for use as an anti-inflammatory agent.

Methods of Making Compounds of the Invention

The compounds of the Invention and their pharmaceutically acceptable salts may be made using the methods as described and exemplified herein and by methods similar thereto and by methods known in the chemical art. Such methods include, but not limited to, those described below. If not commercially available, starting materials for these processes may be made by procedures, which are selected from the chemical art using techniques which are similar or analogous to the synthesis of known compounds.

Various starting materials and/or Compounds of the Invention may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138, and U.S. Pat. No. 9,073,936, the contents of each of which herein are hereby incorporated by reference in their entireties.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. Stable isotopes are nonradioactive isotopes which contain one additional neutron compared to the abundant nuclides of the same species (i.e., element). It is expected that the activity of compounds comprising such isotopes would be retained, and such compound would also have utility for measuring pharmacokinetics of the non-isotopic analogs. For example, the hydrogen atom at a certain position on the Compounds of the Invention may be replaced with deuterium (a stable isotope which is non-radioactive). Examples of known stable isotopes include, but not limited to, deuterium, $^{13}C$, $^{15}N$, $^{18}O$. Alternatively, unstable isotopes, which are radioactive isotopes which contain additional neutrons compared to the abundant nuclides of the same species (i.e., element), e.g., $^{123}I$, $^{131}I$, $^{125}I$, $^{11}C$, $^{18}F$, may replace the corresponding abundant species of I, C and F. Another example of useful isotope of the compound of the invention is the $^{11}C$ isotope. These radio isotopes are useful for radio-imaging and/or pharmacokinetic studies of the compounds of the invention.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks. Solvent mixture compositions are given as volume percentages or volume ratios. In cases where the NMR spectra are complex, only diagnostic signals are reported.

Terms and Abbreviations

BuLi=n-butyllithium
Bu$^t$OH=tert-butyl alcohol,
CAN=ammonium cerium (IV) nitrate,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
LDA=lithium diisopropylamide
MeOH=methanol,
NBS=N-bromosuccinimide
NCS=N-chlorosuccinimide
NaHCO$_3$=sodium bicarbonate,
NH$_4$OH=ammonium hydroxide,
Pd$_2$(dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
TFMSA=trifluoromethanesulfonic acid
THF=tetrahydrofuran.

Methods of Using Compounds of the Invention

The Compounds of the Invention are useful in the treatment of inflammatory diseases or conditions, particularly neuroinflammatory diseases or conditions. Therefore, administration or use of a preferred PDE1 inhibitor as described herein, e.g., a PDE1 inhibitor as hereinbefore described, e.g., a Compound of Formula Ia, Ib, IIa, IIb, III, IV, V, VI, VII, VIII, IX, X, XI, XII provides a means to regulate inflammation (e.g., prevent, reduce, and/or reverse neuroinflammation, and diseases or disorders related to neuroinflammation), and in certain embodiments provide a treatment for various inflammatory diseases and disorders.

For example, in one embodiment the invention provides a method (Method 1) of treatment or prophylaxis of inflammation or disease associated with inflammation comprising administering an effective amount of a specific inhibitor of phosphodiesterase type I (PDE1), to a patient in need thereof, for example:

1.1. Method 1 which is a method of treating neuroinflammation and/or diseases or disorders associated with neuroinflammation and/or microglial function.
1.2. Method 1 or 1.1 wherein the disease or condition to be treated is selected from:
  a. neurodegenerative conditions such as Alzheimer's disease (AD), Parkinson's disease (PD), amyotrophic lateral sclerosis (ALS), and demyelinating conditions, e.g., multiple sclerosis (MS), and prion diseases;
  b. stroke, cardiac arrest, hypoxia, intracerebral hemorrhage or traumatic brain injury;
  c. conditions characterized by abnormal neurotransmitter production and/or response, including depression, schizophrenia, post-traumatic stress disorder, anxiety, attention deficit disorder, and bipolar disease; e.g., wherein any of the foregoing are associated with neuroinflammation; and
  d. chronic CNS infections, e.g., Lyme disease or CNS infection consequent to an immunosuppressive condition, e.g., HIV-dementia;
  e. neuroinflammation consequent to chemotherapy;
    comprising administering an effective amount of a PDE1 inhibitor of the current invention (e.g., a PDE1 inhibitor of Formula I, II, III, IV, V, VI, VII, VIII, IX, X, XI, and/or XII as herein described), e.g., an amount effective to (i) reduce or inhibit activation of M1 microglia, and/or (ii) and amount effective to reduce levels of one or more pro-inflammatory cytokines (e.g., IL1β, TNF-α, and Ccl2, or combination thereof); to a patient in need thereof.
1.3. Any foregoing method wherein the disease or condition to be treated is a neurodegenerative conditions, e.g., selected from Alzheimer's disease (AD), Parkinson's disease (PD), amyotrophic lateral sclerosis (ALS), and demyelinating conditions, e.g., multiple sclerosis (MS), and prion diseases.
1.4. Any foregoing method wherein the disease or condition to be treated is selected from stroke, cardiac arrest, hypoxia, intracerebral hemorrhage and traumatic brain injury.
1.5. Any foregoing method wherein the disease or condition to be treated is a condition characterized by abnormal neurotransmitter production and/or response, e.g., selected from depression, schizophrenia, post-traumatic stress disorder, anxiety, attention deficit disorder, and bipolar disease; e.g., wherein any of the foregoing are associated with neuroinflammation.
1.6. Any foregoing method wherein the disease or condition to be treated is selected from chronic CNS infections, e.g., Lyme disease or CNS infection consequent to an immunosuppressive condition, e.g., HIV-dementia.
1.7. Any foregoing method wherein the disease or condition to be treated is neuroinflammation consequent to chemotherapy.
1.8. Any foregoing method comprising administering an effective amount of a PDE1 inhibitor of the current invention (e.g., a PDE1 inhibitor of Formula I, II, III, IV, V, VI, VII, VIII, IX, X, XI, and/or XII as herein described), e.g., an amount effective to (i) reduce or inhibit activation of M1 microglia, and/or (ii) and amount effective to reduce levels of one or more pro-inflammatory cytokines (e.g., IL1β, TNF-α, IL6 and Ccl2, or combination thereof); to a patient in need thereof.

1.9. Any foregoing method comprising administering an effective amount of a PDE1 inhibitor of the current invention (e.g., a PDE1 inhibitor of Formula I, II, III, IV, V, VI, VII, VIII, IX, X, XI, and/or XII as herein described) to a patient in need thereof, in an amount effective to anti-inflammatory cytokines (e.g., IL-10).

1.10. Any foregoing method comprising administering an effective amount of a PDE1 inhibitor of the current invention (e.g., a PDE1 inhibitor of Formula I, II, III, IV, V, VI, VII, VIII, IX, X, XI, and/or XII as herein described) to a patient in need thereof, in an amount effective to reduce levels of microglial M1 phenotype and/or enhance levels of microglial M2 phenotype.

1.11. Any foregoing method wherein the PDE1 inhibitor is a Compound of Formula Ia, Ib, IIa, IIb, III, IV, V, VI, VII, VIII, IX, X, XI, XII.

1.12. Any foregoing method wherein the neuroinflammation is associated with increased expression and/or activation of microglial cells (e.g., M1 microglial cells) in the brain.

1.13. Any foregoing method wherein the PDE1 inhibitor blunts or inhibits the expression and/or activity of pro-inflammatory cytokines in the brain, e.g., selected from the group consisting of: IL1B, IL-6, TNF-α, Ccl2, Nitric Oxide (NO), and Reactive Oxygen Species (ROS).

1.14. Any foregoing method wherein the PDE1 inhibitor in administered in combination with a PDE4 inhibitor (e.g., rolipram).

1.15. Any foregoing method wherein the patient exhibits increased levels of pro-inflammatory cytokines (e.g., IL1B, IL6, TNF-alpha, Ccl2).

1.16. Any foregoing method wherein "PDE1 inhibitor" describes a compound(s) which selectively inhibit phosphodiesterase-mediated (e.g., PDE1-mediated, especially PDE1B-mediated) hydrolysis of cGMP, e.g., with an $IC_{50}$ of less than 1 μM, preferably less than 750 nM, more preferably less than 500 nM, more preferably less than 50 nM in an immobilized-metal affinity particle reagent PDE assay.

1.17. Any foregoing method wherein the PDE1 inhibitor inhibits the activity of PDE1 (e.g., bovine PDE1 in the assay described in Example 1) with an $IC_{50}$ of less than 10 nM, e.g., wherein the PDE1 inhibitor does not inhibit the activity of PDE types other than PDE1, e.g., has an $IC_{50}$ at least 1000 times greater for PDE types other than PDE1.

1.18. Any foregoing method, wherein the PDE1 inhibitor is selected from any of the following:

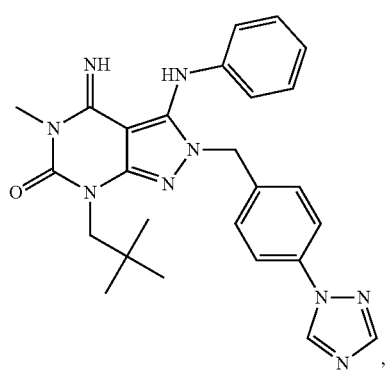

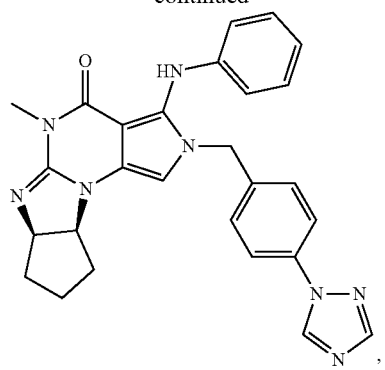

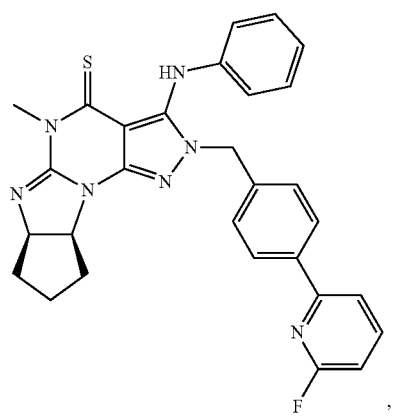

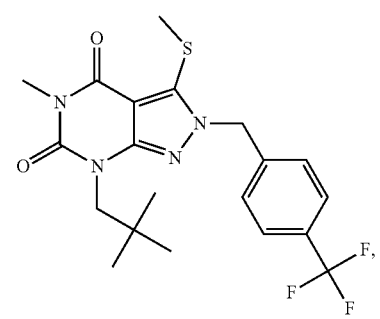

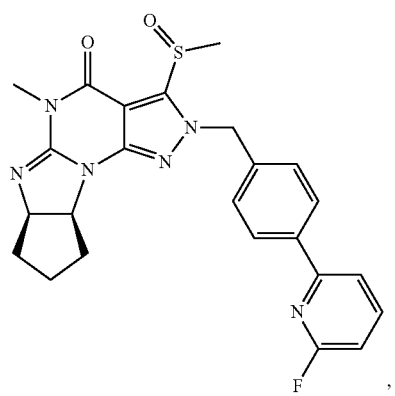

37
-continued
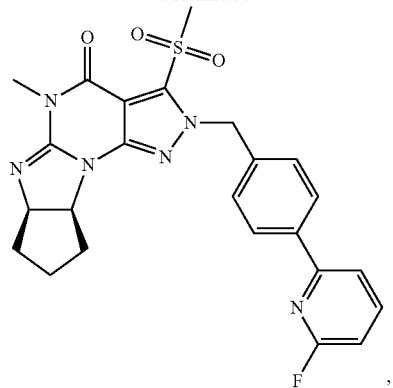
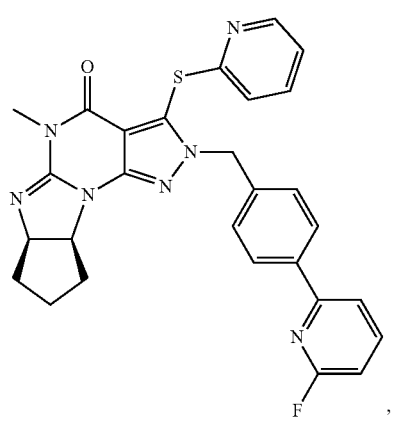
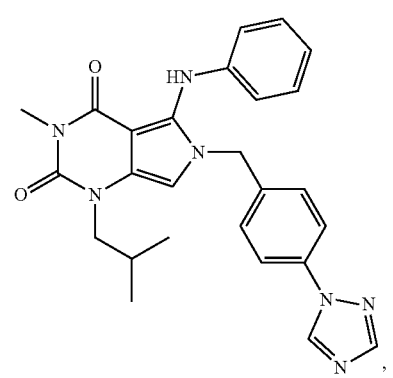
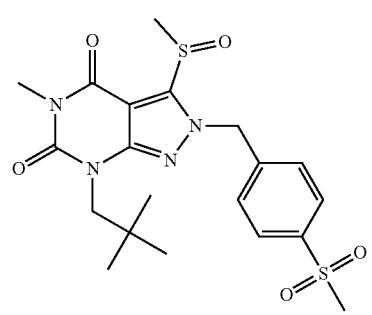
38
-continued
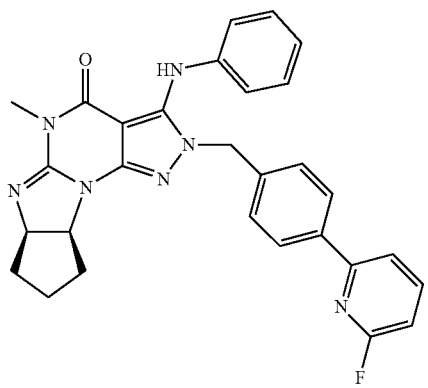
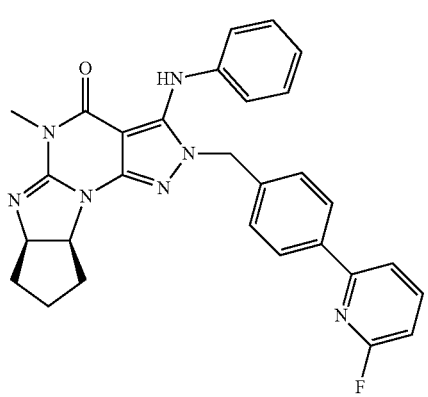
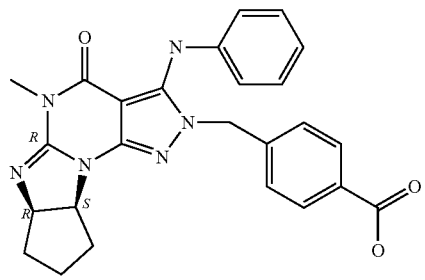

1.19. Any foregoing method, wherein the PDE1 inhibitor is the following:

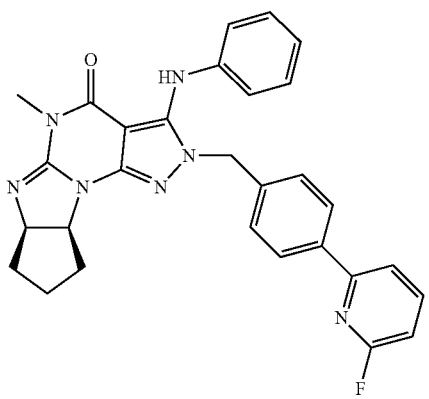 [SMILES: CN1C(=O)c2c(nn(Cc3ccc(-c4cccc(F)n4)cc3)c2Nc2ccccc2)N2C1=N[C@@H]1CCC[C@@H]12]

1.20. Any foregoing method, wherein the PDE1 inhibitor is the following:

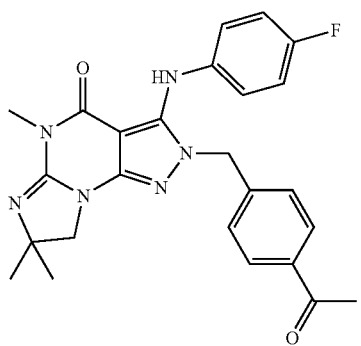 [SMILES: CC(=O)c1ccc(Cn2nc3c(c2Nc2ccc(F)cc2)C(=O)N(C)C2=NC(C)(C)CN23)cc1]

1.21. Any foregoing method, wherein the PDE1 inhibitor is administered in combination (e.g. administered sequentially or simultaneously or within a 24 hour period) with an effective amount of one or more antidepressant agents, e.g., with one or more compounds in free or pharmaceutically acceptable salt form, selected from selective serotonin reuptake inhibitors (SSRIs), serotonin-norepinephrine reuptake inhibitors (SNRIs), tricyclic antidepressants (TCAs), and atypical antipsychotics, e.g. one or more compounds in free or pharmaceutically acceptable salt form, selected from
(a) Selective serotonin reuptake inhibitors (SSRIs), e.g., Citalopram (Celexa), Escitalopram (Lexapro, Cipralex), Paroxetine (Paxil, Seroxat), Fluoxetine (Prozac), Fluvoxamine (Luvox) Sertraline (Zoloft, Lustral);
(b) Serotonin-norepinephrine reuptake inhibitors (SNRIs), e.g., Desvenlafaxine (Pristiq), Duloxetine (Cymbalta), Levomilnacipran (Fetzima), Milnacipran (Ixel, Savella), Tofenacin (Elamol, Tofacine), Venlafaxine (Effexor);
(c) Tricyclic antidepressants (TCAs), e.g., Amitriptyline (Elavil, Endep), Amitriptylinoxide (Amioxid, Ambivalon, Equilibrin), Clomipramine (Anafranil), Desipramine (Norpramin, Pertofrane), Dibenzepin (Noveril, Victoril), Dimetacrine (Istonil), Dosulepin (Prothiaden), Doxepin (Adapin, Sinequan), Imipramine (Tofranil), Lofepramine (Lomont, Gamanil), Melitracen (Dixeran, Melixeran, Trausabun), Nitroxazepine (Sintamil), Nortriptyline (Pamelor, Aventyl), Noxiptiline (Agedal, Elronon, Nogedal), Pipofezine (Azafen/Azaphen), Protriptyline (Vivactil), Trimipramine (Surmontil);
(d) Atypical antipsychotics, e.g., Aripiprazole (Abilify), Asenapine (Saphris), Brexpiprazole (Rexulti), Clozapine (Clozaril), Lumateperone, Lurasidone (Latuda), Olanzapine (Zyprexa), Paliperidone (Invega), Quetiapine (Seroquel), Risperidone (Risperdal), Sertindole (Serdolect, Serlect) Ziprasidone (Geodon)

1.22. Method 1.21 wherein the antidepressant agent is an atypical antipsychotic agent, e.g., Lumateperone, in free or pharmaceutically acceptable salt form.

1.23. Method 1.21 wherein the antidepressant agent is an SSRI, e.g., Fluoxetine or Escitalopram, in free or pharmaceutically acceptable salt form.

1.24. Any of the foregoing method wherein the patient has elevated levels of one or more pro-inflammatory cytokines (e.g., selected from IL1β, TNFα, Ccl2, IL-6, and combinations thereof).

1.25. Any of the foregoing method wherein the patient has reduced levels of one or more anti-inflammatory cytokines (e.g., IL-10).

1.26. Any of the foregoing method wherein the patient has elevated levels of microglial M1 phenotype compared to microglial M2 phenotype.

1.27. Any of the foregoing methods, wherein the patient has abnormal levels (e.g., abnormal levels relative to a reference standard) of one or more of the cytokines described in FIG. 10 or FIG. 11.

1.28. Any of the foregoing methods, wherein the PDE1 inhibitor is administered to treat or prevent chronic neuroinflammation or a disease associated with chronic neuroinflammation.

1.29. Any of the foregoing methods, wherein the PDE1 inhibitor is administered to a patient with an optic nerve injury.

1.30. The method of 1.29, wherein the PDE1 inhibitor increases expression of PDE1 in retinal ganglion.

1.31. The method of 1.29 or 1.30, wherein the administration of the PDE1 inhibitor increases the survival of retinal ganglion cells (e.g., increased as compared to a reference standard or control).

The invention further provides the use of a PDE1 inhibitor, e.g., any of a Compound of Formula I, Formula II, Formula III, Formula IV, Formula V, Formula VI, Formula VII, Formula VIII, Formula IX, Formula X, Formula XI, or Formula XII in the manufacture of a medicament for use in any of Methods 1, et seq.

The invention further provides a PDE1 inhibitor, e.g., any of a Compound of Formula I, Formula II, Formula III, Formula IV, Formula V, Formula VI, Formula VII, Formula VIII, Formula IX, Formula X, Formula XI, or Formula XII for use in any of Methods 1, et seq.

The invention further provides a pharmaceutical composition comprising a PDE1 inhibitor, e.g., any of a Compound of Formula I, Formula II, Formula III, Formula IV, Formula V, Formula VI, Formula VII, Formula VIII, Formula IX, Formula X, Formula XI, or Formula XII for use in any of Methods 1 et seq.

The phrase "Compounds of the Invention" or "PDE 1 inhibitors of the Invention", or like terms, encompasses any and all of the compounds disclosed herewith, e.g., a Compound of Formula I, Formula II, Formula III, Formula IV, Formula V, Formula VI, Formula VII, Formula VIII, Formula IX, Formula X, Formula XI, or Formula XII.

For methods of treatment, the word "effective amount" is intended to encompass a therapeutically effective amount to treat, abrogate, ameliorate, reduce, or mitigate a specific disease or disorder, and/or a symptom thereof, and/or to reduce inflammatory cytokines, e.g., as produced by microglia, and/or to reduce M1 microglia activation, and/or to increase anti-inflammatory cytokines, e.g., as produced by microglia, and/or to enhance M2 microglia activation. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen.

The terms "prevent," "preventing," "prevention," "prophylactic treatment" and the like refer to reducing the probability of developing a disorder or condition in a subject, who does not have, but is at risk of, or susceptible to, developing a disease, disorder, or condition.

By "reduces" is meant a negative alteration of at least 10%, 25%, 50%, 75%, or 100%.

The term "subject" or "patient" refers to an animal which is the object of treatment, observation, or experiment. By way of example only, a subject includes, but is not limited to, a mammal, including, but not limited to, a human or a non-human mammal, such as a non-human primate, murine, bovine, equine, canine, ovine, or feline.

The term "patient" includes a human or non-human (i.e., animal) patient. In a particular embodiment, the invention encompasses both humans and nonhuman animals. In another embodiment, the invention encompasses nonhuman animals. In other embodiments, the term encompasses humans.

The terms "treat," treating," "treatment," and the like refer to reducing or ameliorating a disease or disorder and/or symptoms associated therewith. It will be appreciated that, although not precluded, treating a disease, disorder, or condition does not require that the disease, disorder, condition or symptoms associated therewith be completely eliminated. In some cases "treatment" and "treating" are to be understood as embracing prophylaxis and treatment or amelioration of symptoms of disease, as well as treatment of the cause of the disease.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Any compounds, compositions, or methods provided herein can be combined with one or more of any of the other compositions and methods provided herein.

As used herein, the singular forms "a", "an", and "the" include plural forms unless the context clearly dictates otherwise. Thus, for example, reference to "a cell" includes reference to more than one cell. Unless specifically stated or obvious from context, as used herein, the term "or" is understood to be inclusive.

The term "including" is used herein to mean, and is used interchangeably with, the phrase "including but not limited to."

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Compounds of the Invention, e.g., Formula I, II, III, IV, V, VI, VII, VIII, IX, X, XI, and XII as hereinbefore described, in free or pharmaceutically acceptable salt form, may be used as a sole therapeutic agent, but may also be used in combination or for co-administration with other active agents.

For example, in certain embodiments, the Compounds of the Invention, e.g., Formula I, II, III, IV, V, VI, VII, VIII, IX, X, XI, and XII as hereinbefore described, in free or pharmaceutically acceptable salt form, may be administered in combination (e.g. administered sequentially or simultaneously or within a 24 hour period) with other active agents, e.g., with one or more antidepressant agents, e.g., with one or more compounds in free or pharmaceutically acceptable salt form, selected from selective serotonin reuptake inhibitors (SSRIs),) serotonin-norepinephrine reuptake inhibitors (SNRIs), c) tricyclic antidepressants (TCAs), and atypical antipsychotics.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, by injection, such as intraocular injection, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg (depending on the drug to be administered and the condition to be treated, for example in the case of Compound 214, 0.5 to 25 mg, e.g., 1 to 10 mg, per diem, e.g., in monophosphate salt form, for treatment of neuroinflammatory conditions), conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg (e.g., 1, 2.5, 5, 10, or 20 mg) of a Compound of the Invention, e.g., together with a pharmaceutically acceptable diluent or carrier therefor.

Pharmaceutical compositions comprising Compounds of the Invention may be prepared using conventional diluents or excipients and techniques known in the galenic art. Thus, oral dosage forms may include tablets, capsules, solutions, suspensions and the like.

The present invention further includes pharmaceutical compositions comprising Compounds of the Invention, for example, a PDE1 inhibitor, formulated in pharmaceutically-acceptable or physiologically-acceptable solutions for administration to a cell or an animal, either alone, or in combination with one or more other modalities of therapy.

It will also be understood that, if desired, the compositions, e.g., pharmaceutical compositions, may be administered in combination with other agents as well, such as, various pharmaceutically-active agents, small molecules, polypeptides, or proteins. In the pharmaceutical compositions, formulation of pharmaceutically-acceptable excipients and carrier solutions are well-known to those of skill in the art, as is the development of suitable dosing and treatment regimens for using the particular compositions described herein in a variety of treatment regimens and administration routes, including, for example, without limitation, oral, parenteral, intravenous, subcutaneous, intranasal, intraocular and intramuscular administration and formulations. In certain aspects, pharmaceutically acceptable compositions are provided which comprise a therapeutically-effective amount of a compound as described herein, formulated together with one or more pharmaceutically acceptable carriers (additives) and/or diluents (e.g., pharmaceutically acceptable cell culture medium). Particular embodiments of the invention may compositions and formulations, such as those that are well known in the pharmaceutical art, and that are described, for example, in Remington: The Science and Practice of Pharmacy, 20th Edition. Baltimore, Md.: Lippincott Williams & Wilkins, 2000, or a later edition thereof.

EXAMPLES

Example 1—Effects in the Optic Nerve Injury Model

A PDE1 inhibitory compound was tested in an optic nerve injury model (i.e., the "optic crush" model). The studies described below were carried out using the selective PDE1 inhibitor IC200041, which has the following structure:

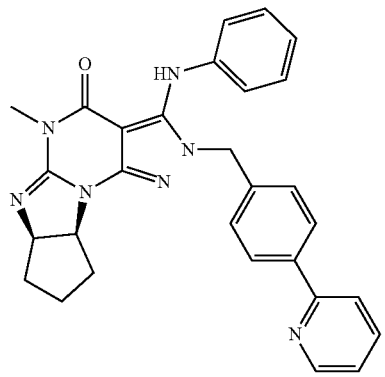 [SMILES: Cn1c(=O)/c(=C(/NCc2ccc(-c3ccccn3)cc2)Nc2ccccc2)c(=N)n2c1=N[C@@H]1CCC[C@@H]12]

In this model, optic nerve surgeries were performed on male mice 8 weeks of age (average body weight, 20-26 g) under general anesthesia, as described previously (Yin Y, et al., Oncomodulin links inflammation to optic nerve regeneration. Proc Natl Acad Sci USA. 2009; 106:19587-19592). Following nerve injury, 3 μl of fluid was removed from the eye and a solution containing the PDE1 inhibitory compound was injected intraocularly.

A total of 4 mouse retinas were treated with the PDE1 inhibitor, and phosphate buffered saline (PBS) was administered to a total of 10 mouse retinas as a control. Mice were typically euthanized with an overdose of anesthesia 14 days after optic nerve injury and were perfused with saline and 4% paraformaldehyde (PFA). These mice were 10 weeks old when killed. Optic nerves and eyes were dissected and postfixed in PFA. Nerves were impregnated with 10% and then 30% sucrose, embedded in OCT Tissue Tek Medium (Sakura Finetek), frozen, cut in the longitudinal plane at a thickness of 14 jam, and mounted on coated slides. Regenerating axons were visualized by staining with a sheep antibody to GAP-43, followed by a fluorescently labeled secondary antibody. Axons were counted manually in at least 8 longitudinal sections per case at pre-specified distances from the injury site, and these numbers were converted into the number of regenerating axons at various distances.

After retinal insult, quantitative analysis showed that PDE expression in retinal ganglion cells was greatly increased. Messenger RNA (mRNA) for PDE1B, in particular, was upregulated about four-fold after injury. RNA was extracted from tissue using standard methods, and mRNA was quantified using quantitative RNAseq sequencing methods. Standard mRNA for beta actin, and four glutamate receptors, namely, NMDA R1 and AMPAK R1, R2 and R3, were evaluated in parallel and showed no significant changes.

The results demonstrated that IC200041 was highly effective in increasing the survival of retinal ganglion cells when compared with the PBS control. Further, the difference in control retinal ganglion cells and those treated with IC200041 were statistically significant. Data obtained from this Example are demonstrated within FIG. 1.

What is claimed is:

1. A method for increasing survival of retinal ganglion cells following optic nerve injury, the method comprising: administering to a patient in need thereof an effective amount of phosphodiesterase 1 (PDE1) inhibitor IC200041, having the following structure:

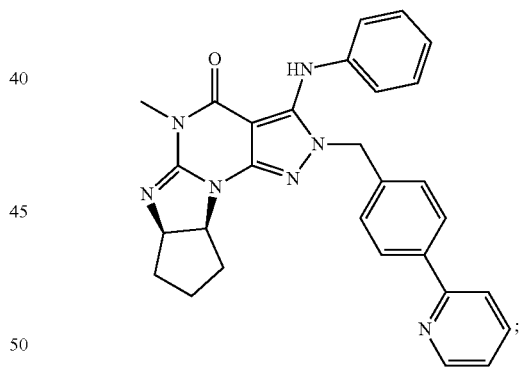

thereby increasing the survival of retinal ganglion cells following the optic nerve injury.

2. The method claim 1, wherein the optic nerve injury comprises retinal insult.

3. The method of claim 1, wherein axonal regeneration is increased following the optic nerve injury.

4. The method of claim 1, wherein administration is by injection.

5. The method of claim 4, wherein administration is by intraocular injection.

* * * * *